(12) United States Patent
Hamersky et al.

(10) Patent No.: US 10,975,339 B2
(45) Date of Patent: *Apr. 13, 2021

(54) ACTIVE AGENT-CONTAINING ARTICLES

(71) Applicant: The Procter & Gamble Company, Cincinnati, OH (US)

(72) Inventors: Mark William Hamersky, Hamilton, OH (US); Mark Robert Sivik, Mason, OH (US); Alessandro Corona, Mason, OH (US); Travis Kyle Hodgdon, Cincinnati, OH (US); Gregory Charles Gordon, Loveland, OH (US); Paul Thomas Weisman, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 150 days.

This patent is subject to a terminal disclaimer.

(21) Appl. No.: 15/975,822

(22) Filed: May 10, 2018

(65) Prior Publication Data
US 2018/0334643 A1 Nov. 22, 2018

Related U.S. Application Data

(60) Provisional application No. 62/506,743, filed on May 16, 2017.

(51) Int. Cl.
| | | |
|---|---|---|
| C11D 17/04 | (2006.01) |
| C11D 11/00 | (2006.01) |
| C11D 3/20 | (2006.01) |
| C11D 3/34 | (2006.01) |
| A61K 8/02 | (2006.01) |

(Continued)

(52) U.S. Cl.
CPC ......... *C11D 17/047* (2013.01); *A61K 8/0208* (2013.01); *A61K 8/342* (2013.01); *A61K 8/416* (2013.01); *A61K 8/8176* (2013.01); *A61K 8/8182* (2013.01); *A61Q 5/12* (2013.01); *C11D 3/2013* (2013.01); *C11D 3/2079* (2013.01); *C11D 3/349* (2013.01); *C11D 11/0017* (2013.01); *C11D 1/62* (2013.01)

(58) Field of Classification Search
CPC ............ C11D 17/04; C11D 11/00; C11D 3/34
See application file for complete search history.

(56) References Cited

U.S. PATENT DOCUMENTS 4,973,422 A * 11/1990 Schmidt ................. C11D 3/505
427/214
5,077,119 A * 12/1991 Wraige ................. C11D 17/047
427/242

(Continued)

OTHER PUBLICATIONS

All Office Actions U.S. Appl. No. 15/975,818.

(Continued)

*Primary Examiner* — Liam J Heincer
*Assistant Examiner* — M. Reza Asdjodi
(74) *Attorney, Agent, or Firm* — C. Brant Cook

(57) ABSTRACT

Active agent-containing articles, for example dryer-added articles and/or washing machine-added articles and/or hair care articles, and more particularly to consumable, single use, water-insoluble articles containing one or more active agents and optionally, one or more auxiliary ingredients, methods for making same, and methods for using same are provided.

19 Claims, 12 Drawing Sheets

(51) Int. Cl.
*A61K 8/34* (2006.01)
*A61K 8/81* (2006.01)
*A61Q 5/12* (2006.01)
*A61K 8/41* (2006.01)
*C11D 1/62* (2006.01)

(56) References Cited

U.S. PATENT DOCUMENTS

| | | | |
|---|---|---|---|
| 7,820,614 B2 | 10/2010 | Tee, Jr. et al. | |
| 8,338,359 B2 | 12/2012 | Kenneally et al. | |
| 9,273,274 B2 | 3/2016 | Aouad et al. | |
| 2003/0195130 A1 | 10/2003 | Lentsch et al. | |
| 2004/0167056 A1 | 8/2004 | Lentsch et al. | |
| 2008/0004204 A1 | 1/2008 | Tindel-Koukal et al. | |
| 2008/0132437 A1* | 6/2008 | Zhang | C11D 1/667 510/102 |
| 2008/0146486 A1* | 6/2008 | Boardman | C11D 3/001 510/519 |
| 2009/0144913 A1* | 6/2009 | Yu | C11D 3/001 8/137 |
| 2011/0023240 A1* | 2/2011 | Fossum | C11D 1/62 8/137 |
| 2012/0021026 A1* | 1/2012 | Glenn, Jr. | A61K 9/70 424/401 |
| 2012/0058166 A1* | 3/2012 | Glenn, Jr. | D01F 1/10 424/401 |
| 2012/0207805 A1* | 8/2012 | Colman | A01N 33/12 424/404 |
| 2015/0004865 A1* | 1/2015 | Soyama | B01D 69/10 442/392 |
| 2015/0126430 A1* | 5/2015 | Ramirez | C11D 1/645 510/513 |
| 2016/0250109 A1* | 9/2016 | Dreher | A61K 8/0216 424/401 |
| 2017/0342348 A1 | 11/2017 | Zhang et al. | |
| 2017/0349859 A1 | 12/2017 | Zhang et al. | |
| 2018/0334643 A1* | 11/2018 | Hamersky | C11D 17/047 |
| 2018/0334644 A1* | 11/2018 | Hamersky | C11D 17/047 |

OTHER PUBLICATIONS

All Office Actions U.S. Appl. No. 15/975,822.
All Office Actions U.S. Appl. No. 15/975,828.
U.S. Appl. No. 15/975,818, filed May 10, 2018, Hodson, et al.
U.S. Appl. No. 15/975,828, filed May 10, 2018, Hamersky, et al.

* cited by examiner

ACTIVE AGENT-CONTAINING ARTICLES

FIELD OF THE INVENTION

The present invention relates to active agent-containing articles, for example dryer-added articles and/or washing machine-added articles and/or hair care articles, and more particularly to consumable, single use, water-insoluble articles containing one or more active agents and optionally, one or more auxiliary ingredients, methods for making same, and methods for using same.

BACKGROUND OF THE INVENTION

Dryer-added articles in the past have consisted of a carrier sheet, such as a thermoplastic nonwoven sheet, for example a polyester nonwoven sheet that is coated and/or impregnated with a fabric conditioning active agent and/or a holder that affixes to a dryer's drum and contains a refillable solid fabric conditioning active agent, often referred to as a dryer bar. During use, the fabric conditioning active agent is at least partially transferred to (deposited on) fabrics from the sheet and/or dryer drum when being treated in a dryer. In the case of the carrier sheet containing the fabric conditioning active agent, remnants of the carrier sheet and/or other remains after use must be disposed above. In the case of the dryer bar, which is a multi-use article, the holder remains affixed to the dryer drum and oftentimes at least a portion of the fabric conditioning active agent remains attached to the holder, since it is a multi-use article.

One problem with existing dryer-added articles is that at least a portion of the existing dryer-added articles and/or holder remains in the dryer after use. In other words, at least a portion of the existing dryer-added articles and/or holder are not consumable after a single use in the dryer. The existing dryer added articles with their excess, not consumed, material creates waste which must be disposed of.

Accordingly, there is a need for an active agent-containing article, for example an active agent-containing dryer-added article that overcomes the negatives described above by being a consumable, single use active agent-containing article, for example a consumable, single use active agent-containing dryer added article, a method for making same, and a method for treating surfaces, such as fabrics with such an active agent-containing article.

SUMMARY OF THE INVENTION

The present invention fulfills the needs described above by providing a consumable, single use active agent-containing article, for example a consumable, single use active agent-containing dryer added article, a method for making same, and a method for using same.

One solution to the problem identified above is to provide a consumable, single use active agent-containing article, for example a consumable, single use active agent-containing dryer added article that is consumed during use for treating fabrics in an automatic clothes dryer and/or in a washing machine wherein the water-insoluble article may form a lamellar structure (exhibit a lamellar structure response) as measured by the Lamellar Structure Test Method described herein and/or a consumable, single use active agent-containing article for treating hair.

In one example of the present invention, a consumable, single use article, for example a consumable, single use, water-insoluble article, such as a fibrous structure and/or film, comprising:

a. one or more active agents; and
b. optionally, one or more auxiliary ingredients;

wherein the article exhibits an Article Density of less than about 0.80 g/cm$^3$ as measured according to the Density Test Method; and wherein the article exhibits a Free Melt Flow of greater than about 20% as measured according to the Free Melt Flow Test Method, is provided.

In another example of the present invention, a method for making a consumable, single use article, for example a consumable, single use, water-insoluble article, such as a fibrous structure and/or film, the method comprising the steps of:

a. providing a filament-forming composition comprising one or more active agents and optionally, one or more auxiliary ingredients; and b. producing a consumable, single use article, for example a consumable, single use, water-insoluble article, such as a fibrous structure and/or film, from the filament-forming composition;

wherein the consumable, single use article exhibits an Article Density of less than about 0.80 g/cm$^3$ as measured according to the Density Test Method; and wherein the consumable, single use article exhibits a Free Melt Flow of greater than about 20% as measured according to the Free Melt Flow Test Method, is provided.

In yet another example of the present invention, a package comprising one or more consumable, single use articles according to the present invention, is provided.

In even yet another example of the present invention, a method for treating surfaces, for example fabrics in need of treatment and/or hair in need of treatment, wherein the method comprises contacting one or more fabrics and/or hair with one or more consumable, single use articles according to the present invention such that the fabrics and/or hair are treated, is provided.

In one example, a method for depositing one or more active agents on a fabric being treated in an automatic clothes dryer, the method comprising the steps of contacting the fabric with one or more active agents from an article according to any of the preceding paragraphs during operation of the dryer is provided.

In another example, a method for depositing one or more active agents on a fabric being treated in a washing machine, the method comprising the steps of contacting the fabric with one or more active agents from an article according to any of the preceding paragraphs during operation of the washing machine is provided.

In another example, a method for depositing one or more active agents on hair being treated in a hair conditioning operation, the method comprising the steps of contacting the hair with one or more active agents from an article according to any of the preceding paragraphs during the hair conditioning operation is provided.

The present invention provides consumable, single use articles, methods for making same, packages containing same, and method for treating surfaces, for example fabric surfaces and/or hair surfaces, with such consumable, single use articles.

Accordingly, the present invention provides active agent-containing articles, for example consumable, single use active agent-containing articles useful for treating fabrics and/or hair, methods for making same, and methods for treating surfaces, such as fabrics and/or hair with such articles.

DETAILED DESCRIPTION OF THE INVENTION

Figure 1:
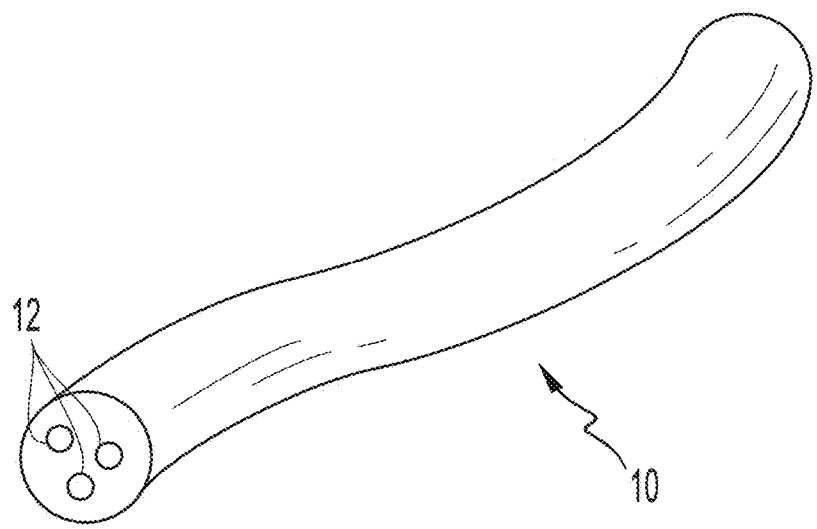
FIG. 1 is a schematic representation of an example of a fibrous element, in this case a filament, according to the present disclosure.

"Article" as used herein refers to a consumer use unit, a consumer unit dose unit, a consumer use saleable unit, a single dose unit, or other use form comprising a unitary fibrous structure and/or film structure and/or comprising one or more fibrous structures and/or film structures of the present invention.

"Fibrous structure" as used herein means a structure that comprises a plurality of fibrous elements and optionally, one or more particles. In one example, a fibrous structure according to the present invention means an association of fibrous elements and optionally, particles that together form a structure, such as a unitary structure, capable of performing a function. Particle may be blended with the fibrous elements, for example in a coform state via a coform process, may be layered between layers or plies of fibrous elements, and/or combinations of these two within a fibrous structure of the present invention and/or article of the present invention.

"Film structure" as used herein means a structure comprising a single component (unlike a fibrous structure comprising a plurality of components; namely, a plurality of fibrous elements) in the form of a continuous or substantially continuous sheet.

The fibrous structures and/or film structures of the present invention may be homogeneous or may be layered. If layered, the fibrous structures and/or film structures may comprise at least two and/or at least three and/or at least four and/or at least five layers, for example one or more fibrous element layers, one or more particle layers and/or one or more fibrous element/particle mixture layers and/or one or more film layers and/or one or more fibrous element layers and one or more film layers. A layer may comprise a particle layer within the fibrous structure and/or films or between fibrous element and/or film layers within a fibrous structure and/or within a multi-layer film structure. A layer comprising fibrous elements and/or a film layer may sometimes be referred to as a ply. A ply may be a fibrous structure and/or a film which may be homogeneous or layered as described herein.

In one example, a single-ply fibrous structure and/or film according to the present invention or a multi-ply fibrous structure and/or multi-ply film comprising one or more fibrous structure plies and/or one or more film structure plies according to the present invention may exhibit a basis weight of less than 5000 g/m$^2$ as measured according to the Basis Weight Test Method described herein. In one example, the single- or multi-ply fibrous structure and/or single- or multi-ply film structure according to the present invention may exhibit a basis weight of greater than 10 g/m$^2$ to about 5000 g/m$^2$ and/or greater than 10 g/m$^2$ to about 3000 g/m$^2$ and/or greater than 10 g/m$^2$ to about 2000 g/m$^2$ and/or greater than 10 g/m$^2$ to about 1000 g/m$^2$ and/or greater than 20 g/m$^2$ to about 800 g/m$^2$ and/or greater than 30 g/m$^2$ to about 600 g/m$^2$ and/or greater than 50 g/m$^2$ to about 500 g/m$^2$ and/or greater than 300 g/m$^2$ to about 3000 g/m$^2$ and/or greater than 500 g/m$^2$ to about 2000 g/m$^2$ as measured according to the Basis Weight Test Method.

In one example, the fibrous structure of the present invention is a "unitary fibrous structure."

"Unitary fibrous structure" as used herein is an arrangement comprising a plurality of two or more and/or three or more fibrous elements that are inter-entangled or otherwise associated with one another to form a fibrous structure and/or fibrous structure plies. A unitary fibrous structure of the present invention may be one or more plies within a multi-ply fibrous structure. In one example, a unitary fibrous structure of the present invention may comprise three or more different fibrous elements. In another example, a unitary fibrous structure of the present invention may comprise two or more different fibrous elements.

"Fibrous element" as used herein means an elongate particulate having a length greatly exceeding its average diameter, i.e. a length to average diameter ratio of at least about 10. A fibrous element may be a filament or a fiber. In one example, the fibrous element is a single fibrous element rather than a yarn comprising a plurality of fibrous elements.

The fibrous elements of the present invention may be spun from filament-forming compositions also referred to as fibrous element-forming compositions via suitable spinning process operations, such as meltblowing, spunbonding, electro-spinning, and/or rotary spinning.

The fibrous elements of the present invention may be monocomponent (single, unitary solid piece rather than two different parts, like a core/sheath bicomponent) and/or multicomponent. For example, the fibrous elements may comprise bicomponent fibers and/or filaments. The bicomponent fibers and/or filaments may be in any form, such as side-by-side, core and sheath, islands-in-the-sea and the like.

In one example as shown in FIG. 1, a fibrous element, for example a filament 10 of the present invention made from a fibrous element-forming composition of the present invention is such that one or more active agents 12 may be present in the filament rather than on the filament, such as a coating composition comprising one or more active agents, which may be the same or different from the active agents in the fibrous elements and/or particles, if present. The total level of fibrous element-forming materials and total level of active agents present in the fibrous element-forming composition may be any suitable amount so long as the fibrous elements of the present invention are produced therefrom.

"Filament" as used herein means an elongate particulate as described above that exhibits a length of greater than or equal to 5.08 cm (2 in.) and/or greater than or equal to 7.62 cm (3 in.) and/or greater than or equal to 10.16 cm (4 in.) and/or greater than or equal to 15.24 cm (6 in.).

Filaments are typically considered continuous or substantially continuous in nature. Filaments are relatively longer than fibers. Non-limiting examples of filaments include meltblown and/or spunbond filaments. Non-limiting examples of polymers that can be spun into filaments include natural polymers, such as starch, starch derivatives, cellulose, such as rayon and/or lyocell, and cellulose derivatives, hemicellulose, hemicellulose derivatives, and synthetic polymers including, but not limited to polyvinyl alcohol and also thermoplastic polymer filaments, such as polyesters, nylons, polyolefins such as polypropylene filaments, polyethylene filaments, and biodegradable thermoplastic fibers such as polylactic acid filaments, polyhydroxyalkanoate filaments, polyesteramide filaments and polycaprolactone filaments.

"Fiber" as used herein means an elongate particulate as described above that exhibits a length of less than 5.08 cm (2 in.) and/or less than 3.81 cm (1.5 in.) and/or less than 2.54 cm (1 in.).

Fibers are typically considered discontinuous in nature. Non-limiting examples of fibers include staple fibers produced by spinning a filament or filament tow of the present invention and then cutting the filament or filament tow into segments of less than 5.08 cm (2 in.) thus producing fibers.

In one example, one or more fibers may be formed from a filament of the present invention, such as when the filaments are cut to shorter lengths (such as less than 5.08 cm in length). Thus, in one example, the present invention also includes a fiber made from a filament of the present invention, such as a fiber comprising one or more filament-forming materials and one or more active agents. Therefore, references to filament and/or filaments of the present invention herein also include fibers made from such filament and/or filaments unless otherwise noted. Fibers are typically considered discontinuous in nature relative to filaments, which are considered continuous in nature.

"Filament-forming composition" and/or "fibrous element-forming composition" and/or "film-forming composition" as used herein means a non-aqueous composition that is suitable for making a fibrous element and/or film of the present invention such as by meltblowing or spunbonding (in the case of fibrous elements) and/or casting or extruding (in the case of films). The filament-forming composition comprises one or more active agents suitable for spinning into a fibrous element and/or casting or extruding into a film. In addition to the one or more active agents, the filament-forming composition may comprise one or more auxiliary ingredients, such as one or more filament-forming materials, for example one or more structurants, that exhibit properties that make them suitable for spinning into a fibrous element and/or casting into a film. In one example, the auxiliary ingredients comprise one or more structurants, such as one or more polymers.

In one example, the filament-forming composition may be made by heating and optionally stirring one or more active agents until the melted active agents are homogeneous. Then the homogeneous melted active agents, which in this case is the filament-forming composition, can be spun into fibrous elements and/or cast or extruded into films. Alternatively, one or more auxiliary ingredients, such as filament-forming materials, for example structurants, such as polymeric structurants and/or inorganic structurants, may be added, with or without stirring and/or agitation, to the homogeneous melted active agents and dissolved, for example homogeneously dissolved, in and/or dispersed, for example homogeneously dispersed, throughout the melted active agents to form the filament-forming composition, which can then be spun into fibrous elements and/or cast or extruded into films.

In one example, a fibrous element, for example a filament of the present invention made from a fibrous element-forming composition of the present invention is such that one or more active agents may be present in the filament rather than on the filament, such as a coating composition comprising one or more active agents, which may be the same or different from the active agents in the fibrous elements and/or particles. The total level of fibrous element-forming materials and total level of active agents present in the fibrous element-forming composition may be any suitable amount so long as the fibrous elements of the present invention are produced therefrom.

Similarly, in one example, a film structure of the present invention made from a film-forming composition of the present invention is such that one or more active agents may be present in the film rather than on the film such as a coating composition comprising one or more active agents, which may be the same or different from the active agents in the film structure. The total level of film-forming materials and total level of active agents present in the film-forming composition may be any suitable amount so long as the film structures of the present invention are produced therefrom.

In one example, one or more active agents, may be present in the fibrous element and/or in the film structure and one or more additional active agents may be present on a surface of the fibrous element and/or film structure as a coating. In another example, a fibrous element of the present invention may comprise one or more active agents that are present in the fibrous element when originally made, but then bloom to a surface of the fibrous element prior to and/or when exposed to conditions of intended use of the fibrous element.

"Filament-forming material" and/or "fibrous element-forming material" as used herein means a material, for example an auxiliary ingredient, such as a structurant, for example a polymer that exhibits properties suitable for making a fibrous element and/or a film. Also, inorganic structurants can act as fillers, viscosity modifiers, and/or to build solid structures, etc. In one example, the filament-forming material is a structurant. A "structurant" as used herein means a material, for example a polymer, that improves the fibrous element spinning of the melted active agents, such as fatty alcohols, fatty quaternary ammonium compounds, fatty acids, etc. The structurant increases the shear and extensional viscosity of the melted active agents to enable fibrous element formation. In one example, the structurant can be included at a level of from about 1 wt % to about 50 wt % and/or from about 1 wt % to about 30 wt % and/or from about 1 wt % to about 10 wt % and/or from about 2 wt % to about 6 wt % and/or from about 3 wt % to about 5 wt % of the filament-forming composition. In one example, the structurant exhibits a weight average molecular weight of from about 10,000 to about 6,000,000 g/mol. The weight average molecular weight is computed by summing the average molecular weights of each polymer raw material multiplied by their respective relative weight percentages by weight of the total weight of polymers present within the article. However, a balance is often struck between concentration and molecular weight, such that when a lower molecular weight species is used, it requires a higher level to result in optimal fibrous element spinning. Likewise, when a higher molecular species is used, lower levels can be used to achieve optimal fibrous element spinning. For example, a structurant having a molecular weight of from about 3,000,000 g/mol to about 5,000,000 g/mol may be included at a level of from about 3 wt % to about 6 wt % whereas a structurant having a molecular weight of from about 50,000 g/mol to about 100,000 g/mol may be included at a level of from about 30 wt % to about 50 wt %. In one example, the structurant is soluble in an oily mixture to enable viscosity build for fibrous element spinning. In addition, the structurant may also be soluble in water to promote removal and to prevent buildup. Suitable structurants include, but are not limited to, polyvinylpyrrolidone, polydimethylacrylamides, and combinations thereof. These polymers are oil (fatty alcohol, fatty acid, fatty quaternary ammonium compounds) soluble, water soluble, water miscible, and capable of being produced at high molecular weights. For example, suitable polymers for use are PVP K120 from Ashland Inc., having a molecular weight of about 3,500,000 g/mol, which is soluble in oil and water and enables fibrous elements to be formed and collected onto a belt. Additional suitable polymers include copolymers of polyvinylpyrrolidone, such as Ganex® or PVP/VA (weight average molecular weight of about 50,000 g/mol) copolymers from Ashland Inc., which also function as suitable structurants but require a higher level to be effective due to their lower molecular weights. In addition, copolymers of polydimethylacrylamide also function as suitable structurants. Hydroxyl propyl cellulose can also function as a suitable structurant.

Non-limiting examples of structurants suitable for the present invention include polymeric structurants, inorganic structurants, and mixtures thereof. In one example, the structurant comprises a polymeric structurant selected from the group consisting of: polylactams such as polyvinylpyrrolidone and copolymers of vinylpyrrolidone, polydimethylacrylamide, copolymers of dimethylacrylamide, and mixtures thereof. In one example, the structurant comprises polyvinylpyrrolidone. In another example, the structurant comprises polydimethylacrylamide. In still another example, the structure comprises polyvinylpyrrolidone and polydimethylacrylamide. In one example, the structurant comprises inorganic structurants selected from the group consisting of clays, silica, and mixtures thereof.

As used herein, "vinyl pyrrolidone copolymer" (and "copolymer" when used in reference thereto) refers to a polymeric structurant of the following structure:

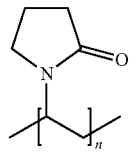

wherein n is an integer such that the polymeric structurant has the degree of polymerization such that it possesses characteristics described herein. For purposes of clarity, the use of the term "copolymer" is intended to convey that the vinyl pyrrolidone monomer can be copolymerized with other non-limiting monomers such as vinyl acetate, alkylated vinyl pyrrolidone, vinyl caprolactam, acrylic acid, methacrylate, acrylamide, methacrylamide, dimethacrylamide, alkylaminomethacrylate, and alkylaminomethacrylamide monomers.

"Particle" as used herein means a solid additive, such as a powder, granule, encapsulate, microcapsule, and/or prill. In one example, the particle exhibits a median particle size of 2000 m or less as measured according to the Median Particle Size Test Method described herein. In another example, the particle exhibits a median particle size of from about 1 μm to about 2000 μm and/or from about 1 μm to about 1600 μm and/or from about 1 μm to about 800 μm and/or from about 5 μm to about 500 μm and/or from about 10 μm to about 300 μm and/or from about 10 μm to about 100 μm and/or from about 10 μm to about 50 μm and/or from about 10 μm to about 30 μm as measured according to the Median Particle Size Test Method described herein. The shape of the particle can be in the form of spheres, rods, plates, tubes, squares, rectangles, discs, stars, fibers or have regular or irregular random forms.

"Active agent-containing particle" as used herein means a solid additive comprising one or more active agents. In one example, the active agent-containing particle is an active agent in the form of a particle (in other words, the particle comprises 100% active agent(s)). The active agent-containing particle may exhibit a median particle size of 2000 μm or less as measured according to the Median Particle Size Test Method described herein. In another example, the active agent-containing particle exhibits a median particle size of from about 1 μm to about 2000 μm and/or from about 1 μm to about 800 μm and/or from about 5 μm to about 500 μm and/or from about 10 μm to about 300 μm and/or from about 10 μm to about 100 μm and/or from about 10 μm to about 50 μm and/or from about 10 μm to about 30 μm as measured according to the Median Particle Size Test Method described herein. In one example, one or more of the active agents is in the form of a particle that exhibits a median particle size of 20 μm or less as measured according to the Median Particle Size Test Method described herein.

In one example of the present invention, the article, for example fibrous structure and/or film structure, comprises a plurality of particles, for example active agent-containing particles, and a plurality of fibrous elements and/or film in a weight ratio of particles, for example active agent-containing particles to fibrous elements and/or film of 1:100 or greater and/or 1:50 or greater and/or 1:10 or greater and/or 1:3 or greater and/or 1:2 or greater and/or 1:1 or greater and/or 2:1 or greater and/or 3:1 or greater and/or 4:1 or greater and/or 5:1 or greater and/or 7:1 or greater and/or 8:1 or greater and/or 10:1 or greater and/or from about 10:1 to about 1:100 and/or from about 8:1 to about 1:50 and/or from about 7:1 to about 1:10 and/or from about 7:1 to about 1:3 and/or from about 6:1 to 1:2 and/or from about 5:1 to about 1:1 and/or from about 4:1 to about 1:1 and/or from about 3:1 to about 1.5:1.

In another example of the present invention, the article, for example a fibrous structure, comprises a plurality of particles, for example active agent-containing particles, and a plurality of fibrous elements in a weight ratio of particles, for example active agent-containing particles, to fibrous elements of from about 10:1 to about 1:1 and/or from about 8:1 to about 1.5:1 and/or from about 7:1 to about 2:1 and/or from about 6:1 to about 2.5:1.

In yet another example of the present invention, the article, for example a fibrous structure, comprises a plurality of particles, for example active agent-containing particles, and a plurality of fibrous elements in a weight ratio of particles, for example active agent-containing particles, to fibrous elements of from about 1:1 to about 1:100 and/or from about 1:15 to about 1:80, and/or from about 1:2 to about 1:60 and/or from about 1:3 to about 1:50 and/or from about 1:3 to about 1:40.

In another example, the article, for example a fibrous structure, of the present invention comprises a plurality of particles, for example active agent-containing particles, at a basis weight of greater than 1 g/m$^2$ and/or greater than 10 g/m$^2$ and/or greater than 20 g/m$^2$ and/or greater than 30 g/m$^2$ and/or greater than 40 g/m$^2$ and/or from about 1 g/m$^2$ to about 5000 g/m$^2$ and/or to about 3500 g/m$^2$ and/or to about 2000 g/m$^2$ and/or from about 1 g/m$^2$ to about 2000 g/m$^2$ and/or from about 10 g/m$^2$ to about 1000 g/m$^2$ and/or from about 10 g/m$^2$ to about 500 g/m$^2$ and/or from about 20 g/m$^2$ to about 400 g/m$^2$ and/or from about 30 g/m$^2$ to about 300 g/m$^2$ and/or from about 40 g/m$^2$ to about 200 g/m$^2$ as measured by the Basis Weight Test Method described herein.

In another example, the article, for example a fibrous structure and/or film structure, of the present invention comprises a plurality of fibrous elements and/or film at a basis weight of greater than 1 g/m$^2$ and/or greater than 10 g/m$^2$ and/or greater than 20 g/m$^2$ and/or greater than 30 g/m$^2$ and/or greater than 40 g/m$^2$ and/or from about 1 g/m$^2$ to about 3000 g/m$^2$ and/or from about 10 g/m$^2$ to about 5000 g/m$^2$ and/or to about 3000 g/m$^2$ and/or to about 2000 g/m$^2$ and/or from about 20 g/m$^2$ to about 2000 g/m$^2$ and/or from about 30 g/m$^2$ to about 1000 g/m$^2$ and/or from about 30 g/m$^2$ to about 500 g/m$^2$ and/or from about 30 g/m$^2$ to about 300 g/m$^2$ and/or from about 40 g/m$^2$ to about 100 g/m$^2$ and/or from about 40 g/m$^2$ to about 80 g/m$^2$ as measured by the Basis Weight Test Method described herein. In one example, the article, for example a fibrous structure and/or film structure, comprises two or more layers wherein fibrous elements and/or film are present in at least one of the layers at a basis weight of from about 1 g/m$^2$ to about 500 g/m$^2$ as measured according to the Basis Weight Test Method described herein.

"Additive" as used herein means any material present in the fibrous element of the present invention that is not a filament-forming material nor an active agent. In one example, an additive comprises a processing aid. In still another example, an additive comprises a filler.

In another example, an additive may comprise a plasticizer for the fibrous element. Non-limiting examples of suitable plasticizers for the present invention include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexanediol, 2,2,4-trimethylpentane-1,3-diol, polyethylene glycol (200-600), pentaerythritol, sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, high fructose corn syrup solids, and dextrins, and ascorbic acid.

In one example, the plasticizer includes glycerin and/or propylene glycol and/or glycerol derivatives such as propoxylated glycerol. In still another example, the plasticizer is selected from the group consisting of glycerin, ethylene glycol, polyethylene glycol, propylene glycol, glycidol, urea, sorbitol, xylitol, maltitol, sugars, ethylene bisformamide, amino acids, and mixtures thereof In another example, an additive may comprise a rheology modifier, such as a shear modifier and/or an extensional modifier. Non-limiting examples of rheology modifiers include but not limited to polyacrylamide, polyurethanes and polyacrylates that may be used in the fibrous elements of the present invention. Non-limiting examples of rheology modifiers are commercially available from The Dow Chemical Company (Midland, Mich.).

In yet another example, an additive may comprise one or more colors and/or dyes that are incorporated into the fibrous elements of the present invention to provide a visual signal when the fibrous elements are exposed to conditions of intended use and/or when an active agent is released from the fibrous elements and/or when the fibrous elements' morphology changes.

In even still yet another example, an additive may comprise one or more anti-blocking and/or detackifying agents. Non-limiting examples of suitable anti-blocking and/or detackifying agents include starches, starch derivatives, crosslinked polyvinylpyrrolidone, crosslinked cellulose, microcrystalline cellulose, silica, metallic oxides, calcium carbonate, talc, mica, and mixtures thereof.

"Conditions of intended use" as used herein means the temperature, physical, chemical, and/or mechanical conditions that an article of the present invention is exposed to when the article is used for one or more of its designed purposes. For example, if an article of the present invention is designed to be used in an automatic clothes dryer and/or in a washing machine for laundry care purposes, the conditions of intended use will include those temperature, chemical, physical and/or mechanical conditions present in an automatic clothes dryer's clothes drying and/or conditioning operation and/or in a washing machine wherein the water-insoluble article may form a lamellar structure (exhibit a lamellar structure response) as measured by the Lamellar Structure Test Method described herein. In another example, if an article of the present invention is designed to be used by a human as a shampoo and/or conditioner for hair care purposes, the conditions of intended use will include those temperature, chemical, physical and/or mechanical conditions present during the shampooing and/or conditioning of the human's hair.

"Active agent" as used herein means a material that produces an intended effect in an environment external to an article of the present invention, such as when the article is exposed to conditions of intended use of the article. In one example, an active agent comprises a material that treats a surface, such as a soft surface (i.e., fabric, hair, skin).

"Treats" as used herein with respect to treating a surface means that the active agent provides a benefit to a surface or environment. Treats includes regulating and/or immediately improving a surface's or environment's appearance, cleanliness, smell, purity and/or feel. In one example treating in reference to treating a keratinous tissue (for example skin and/or hair) surface means regulating and/or immediately improving the keratinous tissue's cosmetic appearance and/or feel. For instance, "regulating skin, hair, or nail (keratinous tissue) condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair. Treats may include providing a benefit to fabrics like during a cleaning or softening in a laundry machine, providing a benefit to hair like during shampooing, conditioning, or coloring of hair, or providing a benefit to environments like a toilet bowl by cleaning or disinfecting it.

In another example, treating means removing stains and/or odors from fabric articles, such as clothes, towels, and linens.

"Fabric care active agent" as used herein means an active agent that when applied to a fabric provides a benefit and/or improvement to the fabric. Non-limiting examples of benefits and/or improvements to a fabric include conditioning, including softening, cleaning (for example by surfactants), stain removal, stain reduction, wrinkle removal, color restoration, static control, wrinkle resistance, permanent press, wear reduction, wear resistance, pill removal, pill resistance, soil removal, soil resistance (including soil release), shape retention, shrinkage reduction, softness, fragrance, anti-bacterial, anti-viral, odor resistance, and odor removal.

"Keratinous tissue active agent" as used herein means an active agent that may be useful for treating keratinous tissue (e.g., hair, skin, or nails) condition. For a hair care active agent, "treating" or "treatment" or "treat" includes regulating and/or immediately improving keratinous tissue cosmetic appearance and/or feel. For instance, "regulating skin, hair, or nail condition" includes: thickening of skin, hair, or nails (e.g., building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair. Another example of keratinous tissue active agent may be an active agent used in the shampooing, conditioning, or dyeing of hair.

"Weight ratio" as used herein means the ratio between two materials on their dry basis. For example, the weight ratio of filament-forming materials to active agents within a fibrous element is the ratio of the weight of filament-forming material on a dry weight basis (g or %) in the fibrous element to the weight of additive, such as active agent(s) on a dry weight basis (g or %—same units as the filament-forming material weight) in the fibrous element. In another example, the weight ratio of particles to fibrous elements within a fibrous structure is the ratio of the weight of particles on a dry weight basis (g or %) in the fibrous structure to the weight of fibrous elements on a dry weight basis (g or %—same units as the particle weight) in the fibrous structure.

"Water-insoluble" with respect to an article and/or material as used herein means an article and/or material of the present invention that does not dissolve in excess water and/or is not miscible in water. In other words, a water-insoluble article when subjected to agitation in excess water may break apart into pieces of the article, but the pieces remain intact in the water. In another example, the article is still water-insoluble even if the article or pieces of the article swell in the excess water so long as the article and/or pieces of the article remain intact. In one example, an article and/or fibrous elements and/or films and/or materials that exhibit a lamellar structure (exhibit a lamellar structure response) as determined according to the Lamellar Structure Test Method are considered water-insoluble herein.

In one example, the article is water-insoluble. As defined herein, water-insoluble means that the article does not completely dissolve or disintegrate when in contact with moisture from the laundered fabrics in the automatic drying process or when in contact with the aqueous wash/rinse bath of the washing process. Where the articles are designed for use in the dryer, water-insoluble auxiliary ingredients, when present, are used instead of water-soluble auxiliary ingredients because water-soluble auxiliary ingredients, which dissolve and/or disintegrate in the presence of water, have the potential to stain or otherwise damage any fabrics being dried in the presence of the articles when they contact a fabric.

"Ambient conditions" as used herein means 23° C.±1.0° C. and a relative humidity of 50%±2%.

"Weight average molecular weight" as used herein means the weight average molecular weight as determined using the industry standard method, gel permeation chromatography.

"Article dimensions," as used herein, refers to the length, width, height, mass, volume, density, and the like, of an article.

"Length," as used herein with respect to a fibrous element, means the length along the longest axis of the fibrous element from one terminus to the other terminus. If a fibrous element has a kink, curl or curves in it, then the length is the length along the entire path of the fibrous element from one terminus to the other terminus. With respect to dimensions of an article, "length" may be defined differently. For example, with respect to articles of irregular shape, the length refers to the maximum feret or caliper diameter, which is the longest distance between two parallel planes tangential to the boundary of the article. For a rectilinear-shaped article, for example, the length refers to the distance from one edge to an opposite edge. In one example, an average length can be provided by measuring ten substantially similar replicate articles, compiling an average of the ten individual article length measurements, and reporting the value to the nearest 0.01 cm, where the individual article length measurements can be taken by any appropriate instrument that is calibrated, NIST traceable, and capable of a measurement to the nearest 0.01 cm. The length of an article, for example, can be measured according to the Width and Length Test Method described herein.

"Diameter" as used herein, with respect to a fibrous element, is measured according to the Diameter Test Method described herein. In one example, a fibrous element of the present invention exhibits a diameter of less than 100 µm and/or less than 75 µm and/or less than 50 µm and/or less than 25 µm and/or less than 20 µm and/or less than 15 µm and/or less than 10 µm and/or less than 6 µm and/or greater than 1 µm and/or greater than 3 µm as measured according to the Diameter Test Method described herein.

"Width," as used herein with respect to dimensions of an article, may refer to the measurement according to its conventional definition. For a rectilinear-shaped article, for example, the width refers to the distance from one edge to an opposite edge. However, with respect to articles of irregular shape, the width refers to the maximum feret or caliper diameter, which is the longest distance between two parallel planes tangential to the boundary of the article. In one example, an average width can be provided by measuring ten substantially similar replicate articles, compiling an average of the ten individual article width measurements, and reporting the value to the nearest 0.01 cm, where the individual article width measurements can be taken by any appropriate instrument that is calibrated, NIST traceable, and capable of a measurement to the nearest 0.01 cm. The width of an article, for example, can be measured according to the Width and Length Test Method described herein.

"Height," as used herein with respect to dimensions of an article, may refer to the measurement according to its conventional definition. The height (thickness), of an article, for example, can be measured according to the Height Test Method described herein.

"Volume," as used herein with respect to dimensions of an article, may refer to the measurement according to its conventional definition. For example, the volume of an article can be calculated by measuring a projected area of the article, as viewed orthogonally to a plane of the length and width of the article, and multiplying the area by the height of the article. In one example, an average volume can be provided by measuring ten substantially similar replicate articles, compiling an average of the ten individual article volume measurements, and reporting the value to the nearest 0.01 cm$^3$. The volume of an article, for example, can be measured according to the Volume Test Method described herein.

"Mass," as used herein with respect to an article, may refer to the measurement according to its conventional definition. For example, the mass of an article can be measured using a top loading analytical balance with a resolution of +0.01 g, where the balance is protected from air drafts and other disturbances by a draft shield. After conditioning the article, the mass of the article can be measured to the nearest 0.01 g. In one example, an average mass can be provided by measuring ten substantially similar replicate articles, compiling an average of the ten individual article mass measurements, and reporting the value to the nearest 0.01 g. The mass of an article, for example, can be measured according to the Mass Test Method described herein.

"Article Density," as used herein with respect to an article, may refer to the measurement according to its conventional definition, such that the article density may be calculated by dividing the mass of the article by its volume. In one example, the article density can be reported to the nearest 0.01 g/cm$^3$. The density of an article, for example, can be measured according to the Density Test Method described herein.

"Triggering condition" as used herein in one example means anything, as an act or event, that serves as a stimulus and initiates or precipitates a change in the article or portion of the article of the present invention, such as a loss or altering of the article's physical structure and/or a release of an active agent therefrom. In another example, the triggering condition may be present in an environment, such as heat within an automatic clothes dryer, when an article of the present invention is added to the automatic clothes dryer and/or when added to a wash liquor, such as water and optionally detergent, with fabrics, for example in a washing machine wherein the water-insoluble article may form a lamellar structure (exhibit a lamellar structure response) as measured by the Lamellar Structure Test Method described herein.

Article

The articles of the present invention may comprise a plurality of fibrous elements, for example a plurality of filaments, such as a plurality of active agent-containing filaments, and/or one or more films, for example one or more active agent-containing films, and optionally, one or more particles, for example one or more active agent-containing particles, such as water-soluble, active agent-containing particles and/or water-insoluble particles, such as zeolites, porous zeolites, perfume-loaded zeolites, active-loaded zeolites, silicas, perfume-loaded silicas, active-loaded zeolites, perfume microcapsules, clays, and mixtures thereof. In certain examples, the article can be substantially formed from non-filament containing structures.

Without wishing to be bound by theory, it is believed that article dimensions can contribute to achieving the most consumer-preferred combination of performance factors of the article, with such factors including consumer-preferred article flexibility, release of active agents such as transfer to clothes in a dryer, compact storage of product, and/or dispensing and does so without leaving behind a carrier sheet or unwanted residue on the treated surfaces, such as fabrics and/or hair. The article and/or product comprising the article may be in the form of a roll (roll form or rolled product), for example multiple articles connected to adjacent sheets by perforation lines for dispensing individual articles from the rolled form wherein the article is convolutely wound upon itself about a core or without a core to form a rolled article. In one example, a multi-article sheet product comprising a plurality of articles separated from adjacent articles by perforation lines is provided. Alternatively, the article may be in the form of discrete, individual sheets or in a non-rolled form of multiple articles connected to adjacent sheets by perforation lines for dispensing individual articles from the non-rolled form. In yet another example, the article of the present invention is a standalone entity ready for use and a collection and/or number of these entities may be distributed to consumers in a product-shipping assembly, for example a protective product-shipping assembly.

Furthermore, it is believed that article dimensions can contribute to achieving a product-shipping assembly that can provide desirable packaging properties, such as minimized packaging sizes, reduced shipping costs, and a maximized ratio of an article volume to a packaging volume, while still providing sufficient protection for the articles. For example, it is believed that providing desirable article dimensions can facilitate reduction of dunnage, thereby reducing costs and waste; improve efficiency in shipping by, for example, providing a shipping container that can fit in a mail slot; and ensure sufficient immobilization and protection of the articles by, for example, minimizing the space in which the article can move within the shipping container.

In certain examples, the article can have a length of from about 1 cm to about 23 cm; from about 2 cm to about 20 cm;

from about 2 cm to about 18 cm; from about 3 cm to about 15 cm; from about 3 cm to about 12 cm; from about 4 cm to about 8 cm; from about 4 cm to about 6 cm; or from about 5 cm to about 6 cm. In certain examples, the article can have a length of from about 1 cm to about 10 cm; from about 2 cm to about 10 cm; or from about 7 cm to about 9 cm as measured according to the Width and Length Test Method described herein.

In certain examples, the article can have a width of from about 1 cm to about 15 cm; from about 2 cm to about 11 cm; from about 2 cm to about 10 cm; from about 3 cm to about 9 cm; from about 4 cm to about 8 cm; or from about 4 cm to about 6 cm as measured according to the Width and Length Test Method described herein. In certain examples, the article can have a width of from about 1 cm to about 6 cm; from about 2 cm to about 6 cm; from about 3 cm to about 5 cm; or from about 3.5 cm to about 4.5 cm as measured according to the Width and Length Test Method described herein. In other examples, the article can have a width of from about 6 cm to about 8 cm as measured according to the Width and Length Test Method described herein.

In certain examples, a ratio of a length of an article to its width can be from about 3:1 to about 0.5:1; from about 5:2 to about 0.5:1; or from about 2:1 to about 1:1 as measured according to the Width and Length Test Method described herein.

The article can have a height, or thickness, of about 0.01 mm or greater; about 0.05 mm or greater; about 0.1 mm or greater; about 0.5 or greater; about 1 mm or greater; about 2 mm or greater; about 3 mm or greater; or about 4 mm or greater as measured according to the Height Test Method described herein. In certain examples, the article can have a height, or thickness, of about 50 mm or less; about 20 mm or less; about 10 mm or less; about 8 mm or less; about 6 mm or less; about 5 mm or less; about 4 mm or less; about 3 mm or less; about 2 mm or less; about 1 mm or less; about 0.5 mm or less; or about 0.3 mm as measured according to the Height Test Method described herein. Thus, in certain examples, the article can have a height from about 0.01 mm to about 50 mm; from about 0.01 to about 44 mm; from about 0.1 mm to about 50 mm; from about 0.1 to about 44 mm; from about 1 mm to about 20 mm; or from about 1 mm to about 5 mm as measured according to the Height Test Method described herein. In certain examples, the article can have a height, or thickness, of from about 3 mm to about 12 mm; or from about 4 mm to about 10 mm as measured according to the Height Test Method described herein.

The article can have a volume of from about 0.25 $cm^3$ to about 60.00 $cm^3$; from about 0.50 $cm^3$ to about 60.00 $cm^3$; from about 0.50 $cm^3$ to about 50.00 $cm^3$; from about 1.00 $cm^3$ to about 40.00 $cm^3$; from about 1.00 $cm^3$ to about 30.00 $cm^3$; from about 2.00 $cm^3$ to about 20.00 $cm^3$; from about 3.00 $cm^3$ to about 20.00 $cm^3$; from about 4.00 $cm^3$ to about 15.00 $cm^3$; or from about 4.00 $cm^3$ to about 10.00 $cm^3$ as measured according to the Volume Test Method described herein. In certain examples, the article can have a volume of from about 3.00 $cm^3$ to about 6.00 $cm^3$ as measured according to the Volume Test Method described herein. In other examples, the article can have a volume of from about 20.00 $cm^3$ to about 35.00 $cm^3$; or from about 24.00 $cm^3$ to about 30.00 $cm^3$ as measured according to the Volume Test Method described herein.

The article can have a mass of about 10 g or less; about 8 g or less; about 6 g or less; about 5 g or less; about 3 g or less; about 2 g or less; about 1 g or less; and/or about 0.10 g or greater and/or about 0.15 g or greater and/or about 0.20 g or greater and/or about 0.40 g or greater and/or 0.50 g or greater as measured according to the Mass Test Method described herein. In certain examples, the article can have a mass of from about 0.10 g to about 10 g; from about 0.10 g to about 8 g; from about 0.1 g to about 6 g; from about 0.15 g to about 5 g; from about 0.20 g to about 3 g; from about 0.20 g to about 2 g; from about 0.20 g to about 1 g as measured according to the Mass Test Method described herein.

The article can have an article density of about 0.05 $g/cm^3$ or greater; about 0.08 $g/cm^3$ or greater; about 0.10 $g/cm^3$ or greater; about 0.15 $g/cm^3$ or greater; about 0.20 $g/cm^3$ or greater; about 0.25 $g/cm^3$ or greater; about 0.30 $g/cm^3$ or greater; about 0.35 $g/cm^3$ or greater; or about 0.40 $g/cm^3$ or greater and/or less than about 0.80 $g/cm^3$ and/or less than about 0.75 $g/cm^3$ and/or less than about 0.70 $g/cm^3$ and/or less than about 0.60 $g/cm^3$ and/or less than 0.50 $g/cm^3$ as measured according to the Density Test Method described herein. In certain examples, the article can have an article density of about 0.80 $g/cm^3$ or less; about 0.60 $g/cm^3$ or less; about 0.50 $g/cm^3$ or less; about 0.40 $g/cm^3$ or less; about 0.35 $g/cm^3$ or less; about 0.30 $g/cm^3$ or less; about 0.25 $g/cm^3$ or less; about 0.20 $g/cm^3$ or less; about 0.15 $g/cm^3$ or less; about 0.12 $g/cm^3$ or less; about 0.10 $g/cm^3$ or less; and/or greater than about 0.08 $g/cm^3$ and/or greater than about 0.05 $g/cm^3$ as measured according to the Density Test Method described herein. Thus, in certain examples, the article can have an article density of from about 0.05 $g/cm^3$ to about 0.80 $g/cm^3$; from about 0.08 $g/cm^3$ to about 0.80 $g/cm^3$; from about 0.1 $g/cm^3$ to about 0.80 $g/cm^3$; from about 0.20 $g/cm^3$ to about 0.60 $g/cm^3$; or from about 0.20 $g/cm^3$ to about 0.40 $g/cm^3$ as measured according to the Density Test Method described herein. In certain examples, the article can have an article density of from greater than about 0.05 $g/cm^3$ to less than about 0.80 $g/cm^3$ and/or from greater than about 0.05 $g/cm^3$ to less than about 0.60 $g/cm^3$ and/or from greater than about 0.05 $g/cm^3$ to less than about 0.30 $g/cm^3$ and/or from greater than about 0.10 $g/cm^3$ to less than about 0.20 $g/cm^3$ as measured according to the Density Test Method described herein.

In certain examples, the article has one or more of the following dimensions: a width from about 1 cm to about 15 cm (as measured according to the Width and Length Test Method described herein); a length from about 1 cm to about 23 cm (as measured according to the Width and Length Test Method described herein); a height from about 0.01 mm to about 50 mm (as measured according to the Height Test Method described herein); a mass from about 0.10 g to about 10 g (as measured according to the Mass Test Method described herein); a volume from about 0.25 $cm^3$ to about 60.00 $cm^3$ (as measured according to the Volume Test Method described herein); and an article density from about 0.05 $g/cm^3$ to about 0.80 $g/cm^3$ (as measured according to the Article Density Test Method described herein). In certain examples, the article has one or more of a width from about 1 cm to about 15 cm (as measured according to the Width and Length Test Method described herein); a length from about 1 cm to about 23 cm (as measured according to the Width and Length Test Method described herein); and a height from about 0.01 mm to about 50 mm (as measured according to the Height Test Method described herein). In certain examples, the article has one or more of a mass from about 0.10 g to about 10 g (as measured according to the Mass Test Method described herein); a volume from about 0.25 $cm^3$ to about 60.00 $cm^3$ (as measured according to the Volume Test Method described herein); and an article density from about 0.05 $g/cm^3$ to about 0.80 $g/cm^3$ (as measured according to the Density Test Method described herein). In certain examples, the article has one or more of a width from about 1 cm to about 15 cm (as measured according to the Width and Length Test Method described herein); a length from about 1 cm to about 23 cm (as measured according to the Width and Length Test Method described herein); and a height from about 0.01 mm to about 50 mm (as measured according to the Height Test Method described herein); and one or more of a mass from about 0.10 g to about 10 g (as measured according to the Mass Test Method described herein); a volume from about 0.25 cm$^3$ to about 60.00 cm$^3$ (as measured according to the Volume Test Method described herein); and an article density from about 0.05 g/cm$^3$ to about 0.80 g/cm$^3$ (as measured according to the Density Test Method described herein).

A product-shipping assembly can include a plurality of articles. In certain examples, each article can include one or more fibrous elements, wherein at least one of the fibrous elements includes one or more filament-forming materials, and one or more active agents releasable from the one or more fibrous elements. In some examples, an article may be substantially formed from non-filament containing structures. Each of the plurality of articles can have dimensions in accordance to those described herein. The product-shipping assembly can further include a shipping container defining an internal volume sized to removably contain the product.

In certain examples, the product-shipping assembly can further include a support member.

In certain examples, the support member can be in contact with the product, and in some examples, the support member can be attached to the product. The support member can support one or more of the plurality of articles and/or facilitate the securement thereof within the shipping container. In one example, the support member can be a tray, where the tray can be sized to fit within the shipping container, such that the plurality of articles may be slidably removed from the shipping container while being substantially contained within the tray. It will be appreciated, however, that a support member may be provided in any of a variety of suitable configurations. The product-shipping assembly may further include one or more dividers, wherein the one or more dividers separate the plurality of articles. In certain examples, the one or more dividers can provide boundaries between multiple compartments within the shipping container, where the plurality of articles can be divided between the multiple compartments, separated by the one or more dividers.

In certain examples, the product-shipping assembly may include a barrier to humidity, liquids (e.g., water), and scent escape. In certain examples, the shipping container can include a protective coating applied to an interior of the shipping container, where the protective coating can serve as the barrier. In one example, the protective coating can be a thin polymeric film. However, it will be appreciated that a protective coating can be any of a variety of suitable coatings known in the art, and the protective coating may be applied through any conventional coating methods known in the art. In certain examples, the protective coating can define the internal volume of the shipping container or be included within the internal volume of the shipping container. The protective coating can be water impermeable, water vapor resistant, and/or scent impermeable.

In other examples, the product-shipping assembly can include one or more overwraps, where the one or more overwraps can serve as the barrier. In certain examples, the one or more overwraps can fully or at least partially wrap an exterior of the shipping container. In certain examples, the one or more overwraps can fully or at least partially cover or surround one or more articles of the plurality of articles. In certain examples, the one or more overwraps can further serve to facilitate the securement of the plurality of articles within the shipping container. In one example, the one or more overwraps can substantially wrap each article, and the overwrap may seal the article therein. The one or more overwraps may be a shrink wrap, a film wrap, a paper wrap, and/or any of a variety of other suitable wraps. Like the protective coating, in certain examples, the one or more overwraps can be water impermeable, water vapor resistant, and/or scent impermeable.

In certain examples, the product-shipping assembly can further include a vent. The vent can allow for off-gassing of, for example, one or more scents, carbon dioxide, oxygen, water vapor, or other gases from the product-shipping assembly. In one example, the vent may include one or more apertures in, for example, a shipping container and/or one or more overwraps.

In certain examples, however, the product-shipping assembly may be substantially dunnage-free, such that the product-shipping assembly may include minimal excessive protective packaging materials, such as bubble wrap, Styrofoam, and the like, or be completely free thereof. In one example, a ratio of a volume of the plurality of articles to the internal volume can be about 0.8 or greater. In certain examples, the ratio of the volume of the plurality of articles to the internal volume can be about 0.85 or greater; about 0.9 or greater; or about 0.95 or greater.

The shipping container can be any package, box, carton, bag, wrap, or other conventional type of receptacle used in the packing and distribution of products, as described above. In particular, the shipping container can be suitable for use in e-commerce. In one example, the shipping container can have a width of about 6 inches or less; a length of about 10 inches or less; and a height of about 1.75 inches or less. In such an example, the shipping container may be sized and shaped to fit into a conventional mail slot. It will be appreciated, however, that a shipping container can be provided in any of a variety of suitable sizes, shapes, and configurations.

The plurality of articles may include from about 2 articles to about 144 articles, and any amount of articles in between. For example, the plurality of articles can include about 2 articles or more; about 8 articles or more; about 12 articles or more; about 18 articles or more; about 24 articles or more; about 25 articles or more; about 30 articles or more; about 36 articles or more; about 40 articles or more; about 48 articles or more; about 50 articles or more; about 60 articles or more; or about 64 articles or more. In certain examples, at least two articles of the plurality of articles can have different scents.

The product-shipping assembly can further include a water scavenging material. In one example, the water scavenging material can be a desiccant. However, it will be appreciated that the water scavenging material can be any of a variety of suitable water scavenging materials known in the art.

In one example, the fibrous elements and/or particles may be arranged within the fibrous structure and thus an article comprising the fibrous structure to provide the article with two or more regions or layers that comprise different active agents. For example, one region of the article may comprise anti-static agents and another region of the article may comprise fabric conditioning active agents.

With respect to an article including one or more fibrous elements, the fibrous elements and/or fibrous structures of the present invention are in solid form. However, the filament-forming composition used to make the fibrous elements of the present invention may be in the form of a liquid.

In one example, the fibrous structure comprises a plurality of identical or substantially identical from a compositional perspective of fibrous elements according to the present invention.

In another example, the fibrous structure may comprise two or more different fibrous elements according to the present invention. Non-limiting examples of differences in the fibrous elements may be physical differences such as differences in diameter, length, texture, shape, rigidness, elasticity, and the like; chemical differences such as cross-linking level, solubility, melting point, Tg, active agent, filament-forming material, color, level of active agent, basis weight, level of filament-forming material, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. In one example, two or more fibrous elements and/or particles within the fibrous structure may comprise different active agents. This may be the case where the different active agents may be incompatible with one another, for example an anionic surfactant (such as a shampoo active agent) and a cationic surfactant (such as a hair conditioner active agent).

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

In one example, the fibrous structure may comprise discrete regions of fibrous elements that differ from other parts of the fibrous structure.

The fibrous structure of the present invention may be used as is or may be coated with one or more active agents.

In one example, a fibrous structure can exhibit a thickness of greater than 0.01 mm and/or greater than 0.05 mm and/or greater than 0.1 mm and/or to about 50 mm and/or to about 20 mm and/or to about 10 mm and/or to about 5 mm and/or to about 2 mm and/or to about 0.5 mm and/or to about 0.3 mm as measured by the Thickness Test Method described herein.

Non-limiting examples of other fibrous structures suitable for the present invention are disclosed in U.S. Published Patent Application No. 2013/0171421 A1 and U.S. Pat. No. 9,139,802 are hereby incorporated by reference herein.

The articles of the present invention may exhibit one or more of the following properties.

In one example, the articles and/or fibrous elements and/or films of the present invention may exhibit a lamellar structure (exhibit a lamellar structure response) upon wetting as determined by the Lamellar Structure Test Method described herein.

In one example, the articles and/or fibrous elements and/or films of the present invention may exhibit a lamellar structure (exhibit a lamellar structure response) upon wetting as determined by the Lamellar Structure Test Method described herein, but does not exhibit a lamellar structure (exhibit a lamellar structure response) in a conditioned only, dry state as determined by the Lamellar Structure Test Method.

In one example, the articles of the present invention may exhibit an Air Permeability of at least 20 and/or at least 40 and/or at least 60 and/or at least 80 and/or less than 7000 and/or less than 6000 and/or less than 5000 and/or less than 4000 and/or less than 3000 and/or less than 2000 $L/m^2/s$ as measured according to the Air Permeability Test Method described herein.

In one example, the articles of the present invention may exhibit a Free Melt Flow of greater than about 20% and/or greater than about 30% and/or greater than about 40% and/or greater than about 50% and/or greater than about 60% and/or greater than about 70% and/or greater than about 80% and/or greater than about 85% and/or greater than about 90% and/or greater than about 95% and/or greater than about 97% and/or greater than about 98% and/or greater than about 99% and/or about 100% as measured according to the Free Melt Flow Test Method described herein. In one example, the articles of the present invention may exhibit a Free Melt Flow of from about 20% to about 100% and/or from about 30% to about 100% and/or from about 40% to about 100% and/or from about 50% to about 100% and/or from about 60% to about 99% and/or from about 70% to about 99% and/or from about 80% to about 99% and/or from about 90% to about 99% as measured according to the Free Melt Flow Test Method described herein.

In one example, the article is a non-woven comprising a fibrous structure comprising one or more fibrous elements, for example a plurality of filaments. The article may comprise two or more nonwovens, a multi-ply nonwoven and/or multi-ply fibrous structure and/or multi-ply film.

In one example, the article, for example fibrous structure and/or film, may comprise one or more apertures.

In one example, the article exhibits a geometric mean peak elongation of about 5% or greater as measured according to the Tensile Test Method.

In one example, the article exhibits a geometric mean modulus of about 5000 g/cm or less as measured according to the Tensile Test Method.

In one example, the article exhibits a geometric mean tensile strength of about 100 g/in or more according to the Tensile Test Method.

In one example, the article exhibits a water content of from about 0% to about 20% and/or from about 0% to about 5% as measured according to the Water Content Test Method. In one example, the article exhibits a water content of from about 2% to about 15% and/or from about 2% to about 10% and/or from about 5% to about 10% as measured according to the Water Content Test Method.

In one example, the article comprises adhesive or a material that functions as an adhesive, for example on one or more surfaces of the article to attach the article to an automatic clothes dryer internal drum surface.

In one example, during use of the article in an automatic clothes dryer operation, the article transfers (deposits) at least a portion, and/or substantially all of its mass to fabrics being treated, for example dried and/or conditioned, in the automatic clothes dryer.

In one example, during use of the article in a washing machine operation, the article transfers (deposits) at least a portion, and/or substantially all of its mass to fabrics being treated, for example washed and/or conditioned, in the washing machine.

In one example, the fibrous elements and/or particles may be arranged within the fibrous structure to provide the fibrous structure with two or more regions or layers that comprise different active agents. For example, one region of the fibrous structure may comprise bleaching agents and/or surfactants and another region of the fibrous structure may comprise softening agents.

Figure 2:
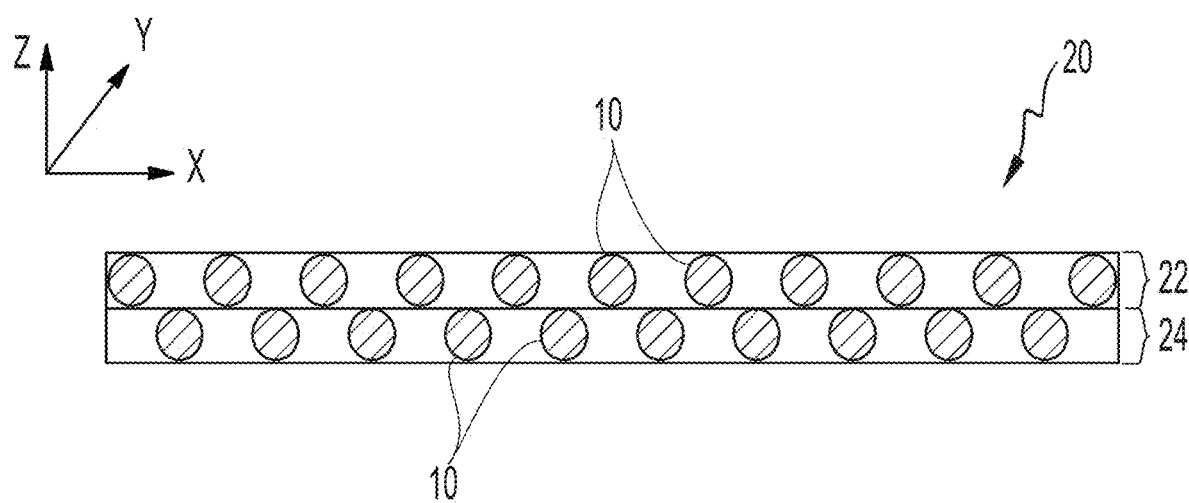
FIG. 2 is a schematic representation of an example of a fibrous structure comprising a plurality of filaments according to the present disclosure.
Figure 3:
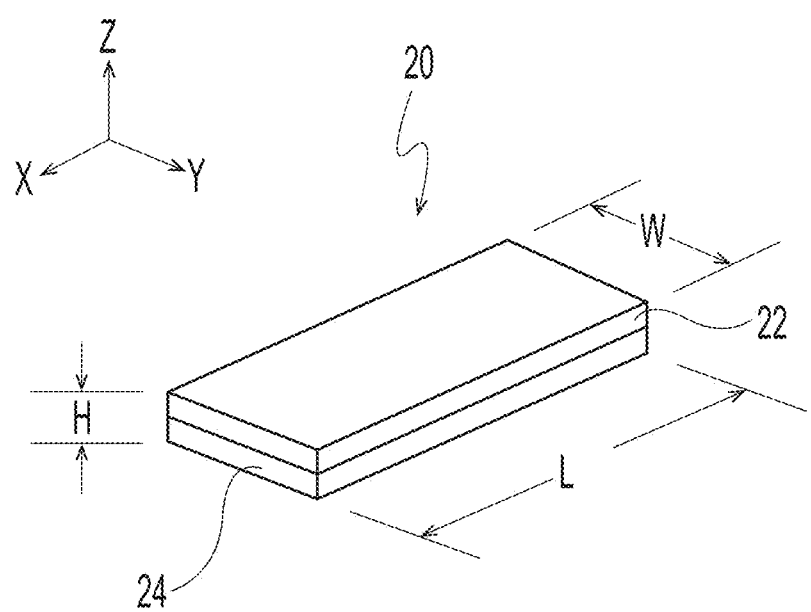
FIG. 3 is another schematic representation of the article of FIG. 2, depicting article dimensions.

As shown in FIG. 2, an example of an article 20 of the present invention, for example a multi-ply fibrous structure according to the present invention may comprise two or more different fibrous structure layers or plies 22, 24 (in the z-direction of the article 20 of fibrous elements, in this case filaments, 10 of the present invention that form the fibrous structures of the article 20. The filaments 10 in layer 22 may be the same as or different from the filaments 10 in layer 24. Each layer or ply 22, 24 may comprise a plurality of identical or substantially identical or different filaments. For example, filaments that may release their active agents at a faster rate than others within the article 20 and/or one or more fibrous structure layers or plies 22, 24 of the article 20 may be positioned as an external surface of the article 20. The layers or plies 22 and 24 may be associated with each other by mechanical entanglement at their interface between the two layers or plies and/or by thermal or adhesive bonding and/or by depositing one of the layers or plies onto the other existing layer or ply, for example spinning the fibrous elements of layer or ply 22 onto the surface of the layer or ply 24. FIG. 3 shows another view of the article 20, with plies 22 and 24. With respect to the article dimensions described above, the length (L), width (W), and height (H) of the article are shown in FIG. 3 to correspond to measurements in the x-, y-, and z-directions, respectively, and are measured according to the Width and Length Test Method and the Height Test Method described herein.

Figure 4:
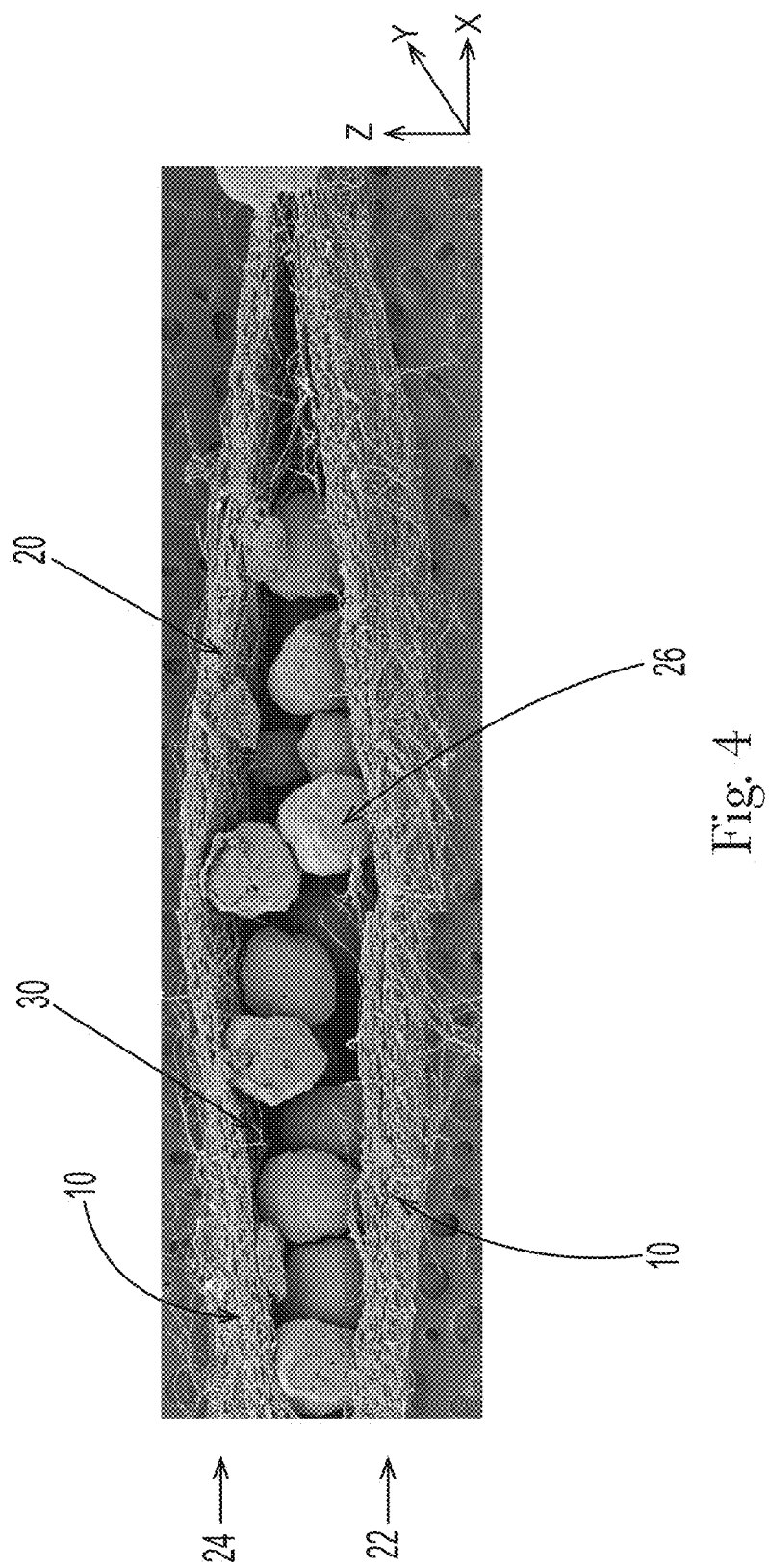
FIG. 4 is a scanning electron microscope photograph of a cross-sectional view of an example of a fibrous structure according to the present disclosure.

As shown in FIG. 4, another example of an article 20, for example a fibrous structure according to the present invention comprises a first fibrous structure layer or ply 22 comprising a plurality of fibrous elements, for example filaments 10, a second fibrous structure layer 24 comprising a plurality of fibrous elements, for example filaments 10, and a plurality of particles or a particle layer 26 positioned between the first and second fibrous structure layers 22 and 24. A similar fibrous structure can be formed by depositing a plurality of particles on a surface of a first ply of fibrous structure comprising a plurality of fibrous elements and then associating a second ply of fibrous structure comprising a plurality of fibrous elements such that the particles or a particle layer are positioned between the first and second fibrous structure plies.

Figure 5:
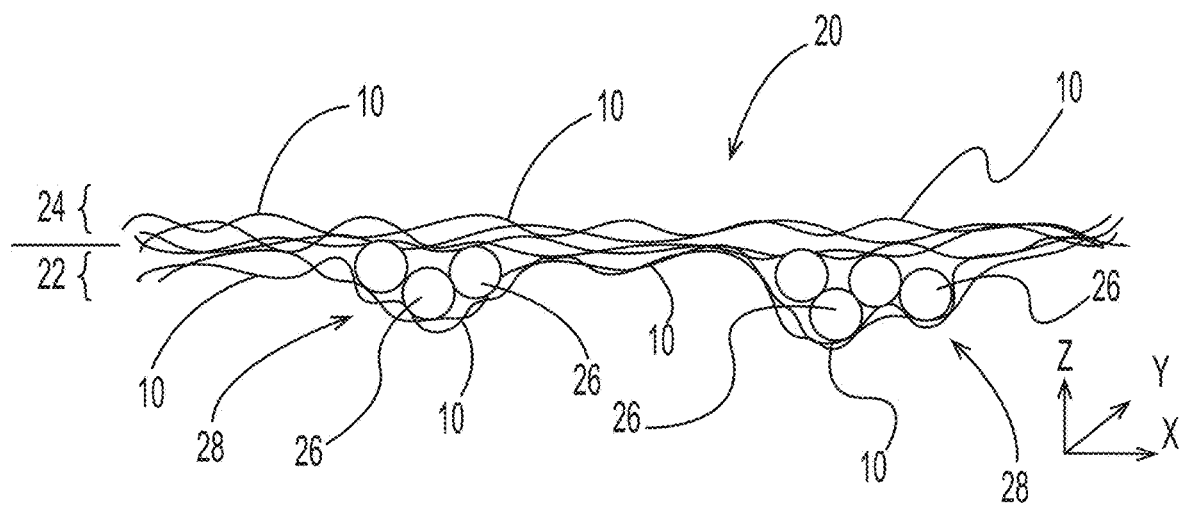
FIG. 5 is a schematic representation of a cross-sectional view of another example of a fibrous structure according to the present disclosure.

As shown in FIG. 5, another example of an article 20, for example a fibrous structure of the present invention comprises a first fibrous structure layer 22 comprising a plurality of fibrous elements, for example filaments 10, wherein the first fibrous structure layer 22 comprises one or more pockets 28 (also referred to as recesses, unfilled domes, or deflected zones), which may be in an irregular pattern or a non-random, repeating pattern. One or more of the pockets 28 may contain one or more particles 26. The article 20 in this example further comprises a second fibrous structure layer 24 that is associated with the first fibrous structure layer 22 such that the particles 26 are entrapped in the pockets 28. Like above, a similar article can be formed by depositing a plurality of particles in pockets of a first ply of fibrous structure comprising a plurality of fibrous elements and then associating a second ply of fibrous structure comprising a plurality of fibrous elements such that the particles are entrapped within the pockets of the first ply. In one example, the pockets may be separated from the fibrous structure to produce discrete pockets.

Figure 6:
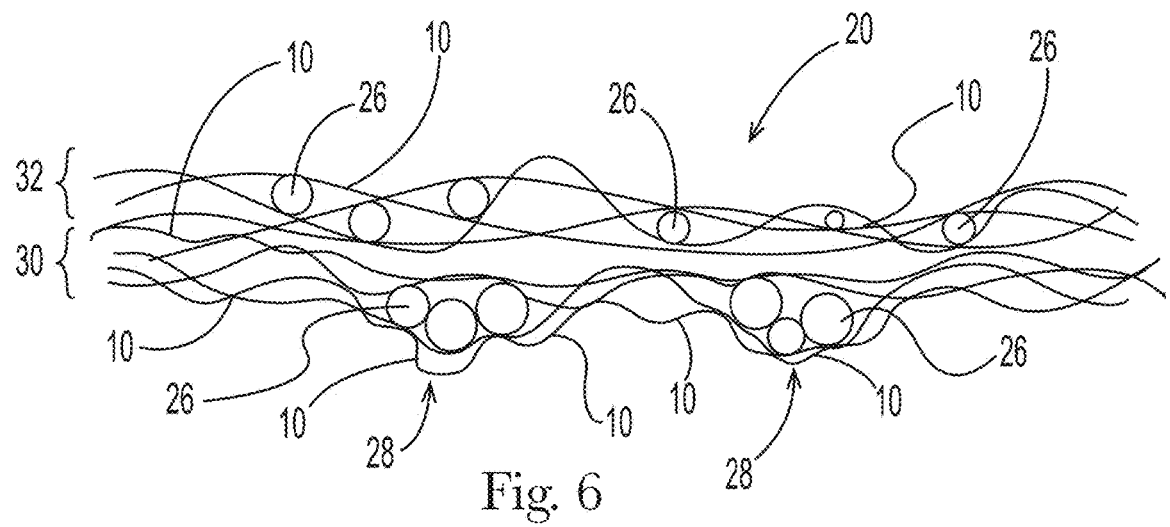
FIG. 6 is a schematic representation of a cross-sectional view of another example of a fibrous structure according to the present disclosure.

As shown in FIG. 6, another example of an article 20, for example a multi-ply fibrous structure of the present invention comprises a first ply 30 of a fibrous structure according to FIG. 5 above and a second ply 32 of fibrous structure associated with the first ply 30, wherein the second ply 32 comprises a plurality of fibrous elements, for example filaments 10, and a plurality of particles 26 dispersed, in this case randomly, in the x, y, and z axes, throughout the article 20.

Figure 7:
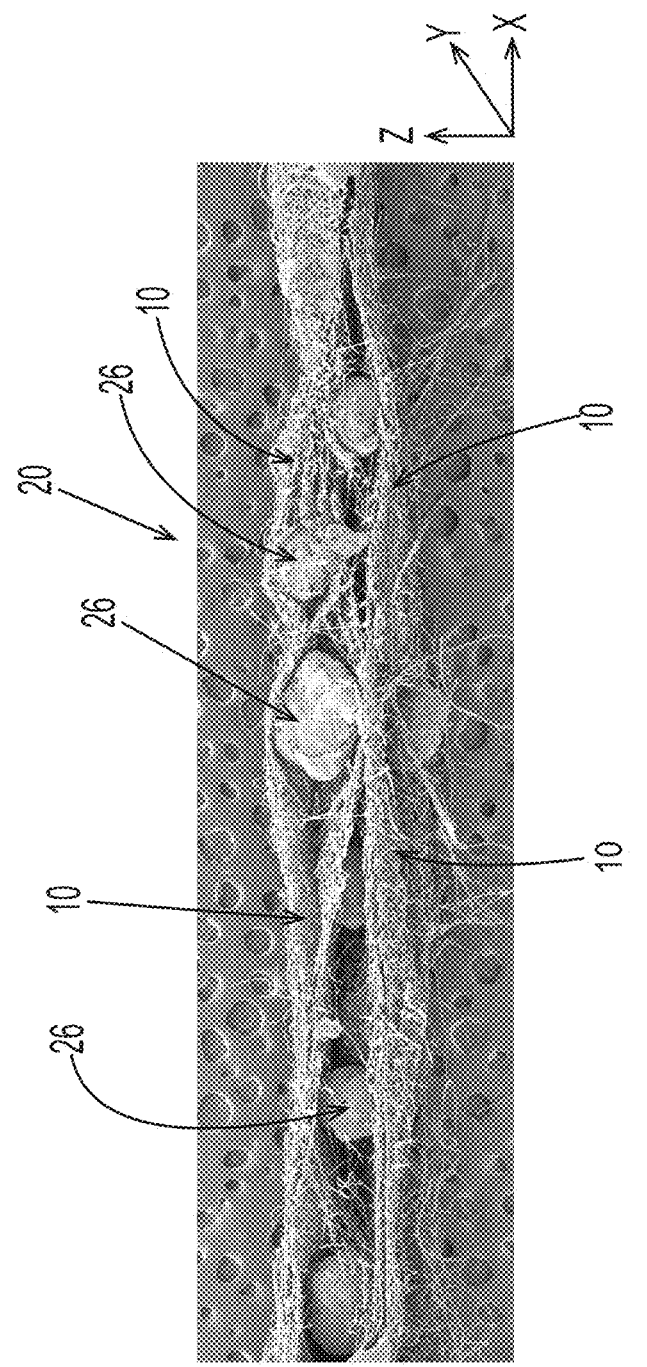
FIG. 7 is a scanning electron microscope photograph of a cross-sectional view of another example of a fibrous structure according to the present disclosure.

As shown in FIG. 7, another example of an article 20, for example a fibrous structure of the present invention comprises a plurality of fibrous elements, for example filaments 10, such as active agent-containing filaments, and a plurality of particles 26, for example active agent-containing particles, dispersed, in this case randomly, in the x, y, and z axes, throughout the fibrous structure of the article 20.

Figure 8:
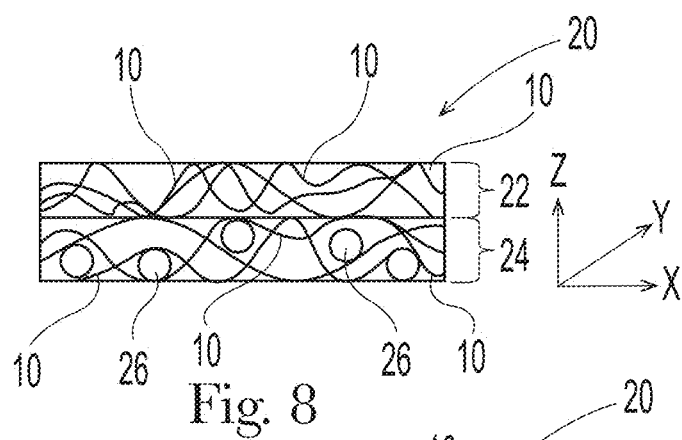
FIG. 8 is a schematic representation of a cross-sectional view of another example of a fibrous structure according to the present disclosure.

As shown in FIG. 8, another example of an article 20, for example a fibrous structure of the present invention comprises a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24. Alternatively, in another example, the plurality of particles 26, for example active agent-containing particles, may be dispersed in an irregular pattern or a non-random, repeating pattern within the second fibrous structure layer 24. Like above, a similar article comprising two plies of fibrous structure comprising a first fibrous structure ply 22 comprising a plurality of fibrous elements, for example filaments 10, and a second fibrous structure ply 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure ply 24. Alternatively, in another example, the plurality of particles 26, for example active agent-containing particles, may be dispersed in an irregular pattern or a non-random, repeating pattern within the second fibrous structure ply 24.

Figure 9:
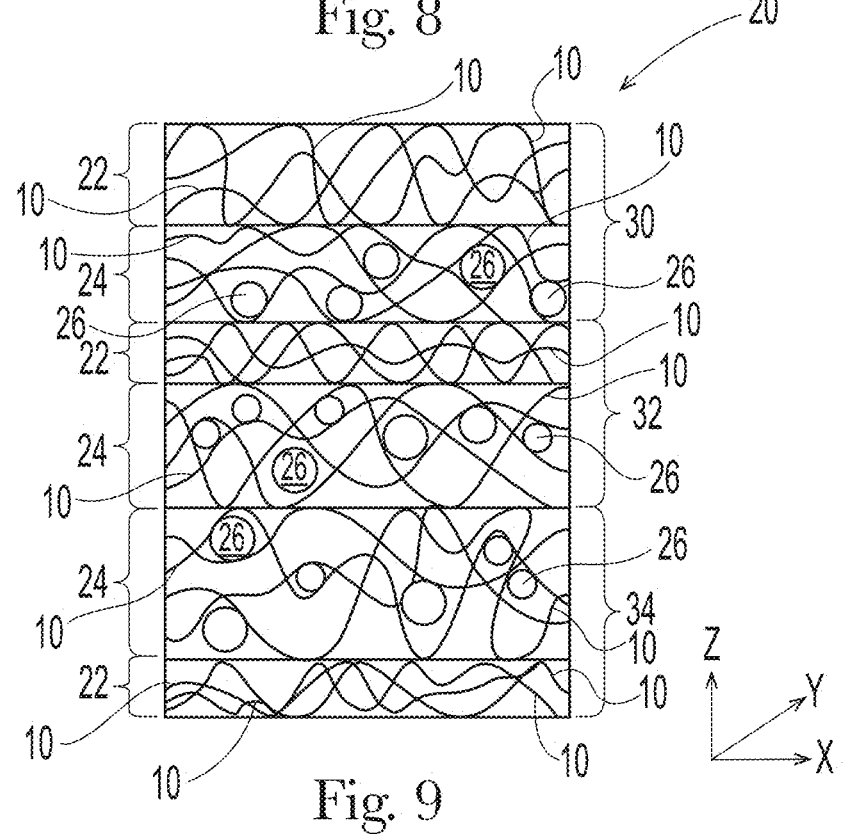
FIG. 9 is a schematic representation of a cross-sectional view of another example of a fibrous structure according to the present disclosure.

FIG. 9 shows another example of an article 20, for example a multi-ply fibrous structure of the present invention comprising a first ply 30 of a fibrous structure as shown in FIG. 8 comprising a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24, a second ply 32 of a fibrous structure associated with the first ply 30, wherein the second ply 32 comprises a first fibrous structure layer 22 comprising a plurality of fibrous elements, for example filaments 10, and a second layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24, and a third ply 34 of a fibrous structure associated with the second ply 32, wherein the third ply 34 comprises a first fibrous structure layer 22 comprising a plurality of fibrous elements, for example filaments 10, and a second fibrous structure layer 24 comprising a plurality of fibrous elements, for example filaments 10, for example active agent-containing filaments, and a plurality of particles 26, for example active agent-containing particles, dispersed, in this case randomly, in the x, y, and z axes, throughout the second fibrous structure layer 24.

Figure 10:
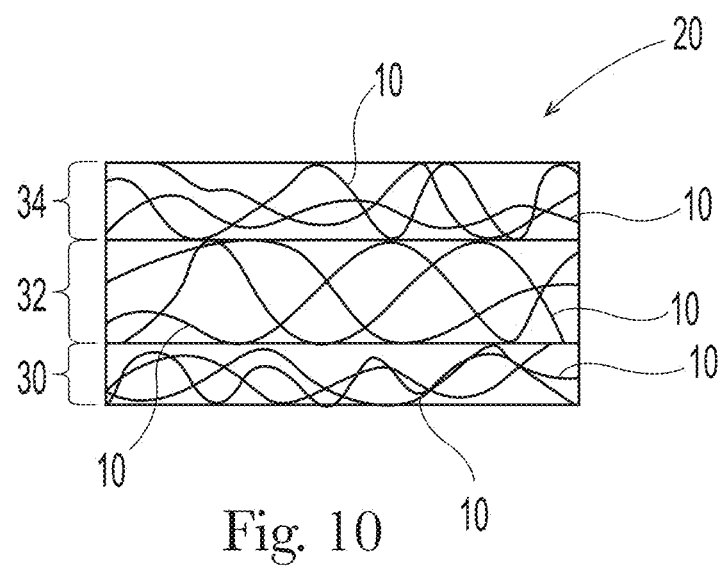
FIG. 10 is a schematic representation of a cross-sectional view of another example of a fibrous structure according to the present disclosure.

As shown in FIG. 10, another example of an article 20, for example a multi-ply fibrous structure of the present invention comprises a first ply 30 of a fibrous structure comprising a plurality of fibrous elements, for example filaments 10, a second ply 32 of a fibrous structure associated with the first ply 30, wherein the second ply 32 comprises a plurality of fibrous elements, for example filaments 10, and a third ply 34 of a fibrous structure associated with the second ply 32, wherein the third ply 34 comprises a plurality of fibrous elements, for example filaments 10. In one example of FIG. 10, each ply's filaments 10 may comprise active agent-containing filaments.

Figure 11:
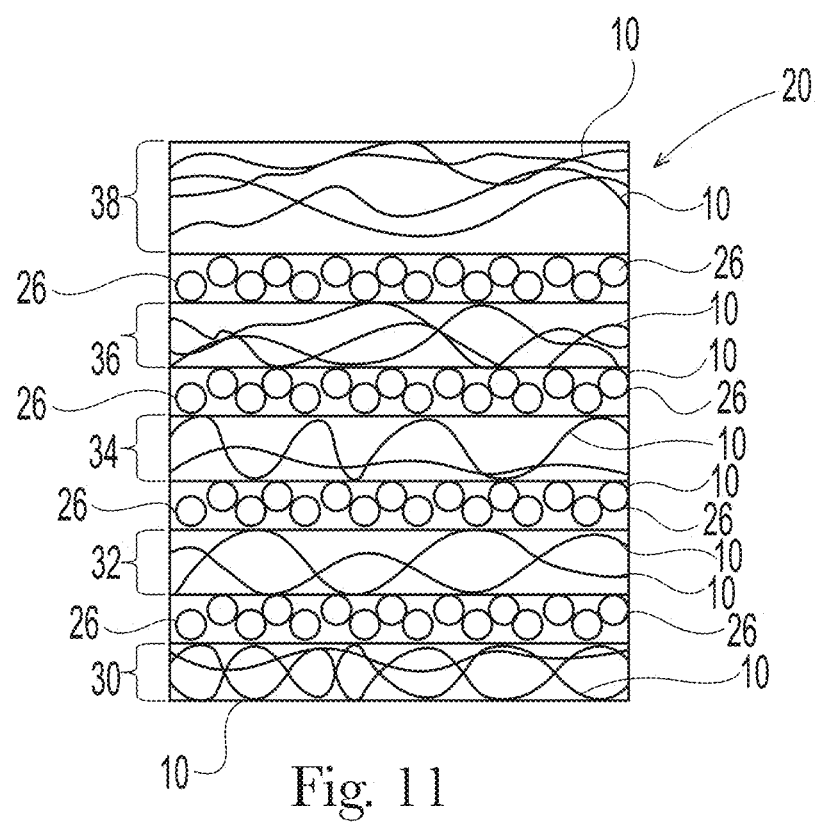
FIG. 11 is a schematic representation of a cross-sectional view of another example of a fibrous structure according to the present disclosure.

FIG. 11 shows another example of an article 20 multi-ply fibrous structure 20 of the present invention comprising a first ply 30 of a fibrous structure comprising a plurality of fibrous elements, for example filaments 10, a second ply 32 of fibrous structure comprising a plurality of fibrous elements, for example filaments 10, a third ply 34 of a fibrous structure comprising a plurality of fibrous elements, for example filaments 10, a fourth ply 36 of fibrous structure comprising a plurality of fibrous elements, for example filaments 10, and a fifth ply 38 of a fibrous structure comprising a plurality of fibrous elements, for example filaments 10. In this example, the article 20 further comprises one or more particles or particle layers 26 positioned between at least two adjacent fibrous structure plies, for example plies 30 and 32 or plies 32 and 34 or plies 34 and 36 or plies 36 and 38. The plies 30, 32, 34, 36, and 38 are associated with one or more other plies to form a unitary structure and to minimize particles 26, if any are present within the article 20, from becoming disassociated from the article 20. In another example, the one or more particles or particle layers 26 positioned between at least two adjacent fibrous structure plies are present in an irregular pattern, a non-random, repeating pattern, or only in select zones between the plies.

Figure 12:
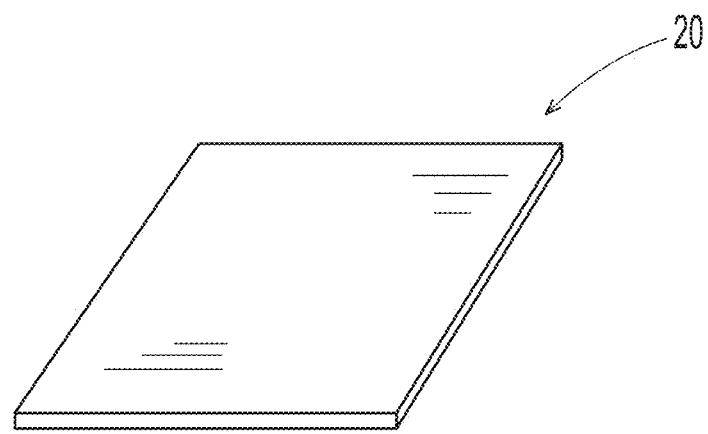
FIG. 12 is a schematic representation of an example of a film structure according to the present invention.

As shown in FIG. 12, another example of an article 20, for example a film structure of the present invention comprises a film structure comprising one or more active agents.

Figure 13:
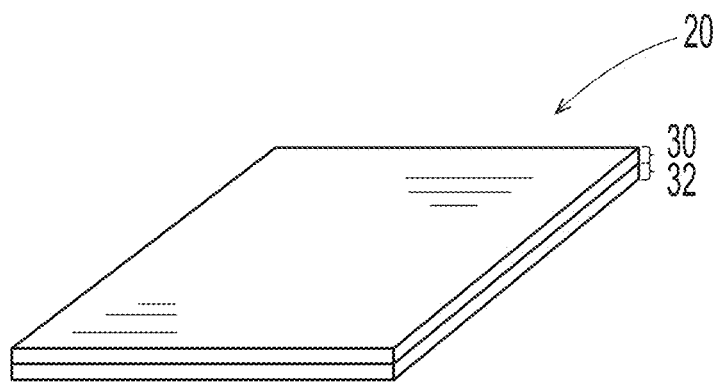
FIG. 13 is a schematic representation of another example of a film structure according to the present invention.

As shown in FIG. 13, another example of an article 20, for example a multi-ply film structure of the present invention comprises a first ply 30 of a film structure and a second ply 32 of a film structure associated with the first ply 30, wherein at least one of the first and second plies 30, 32 comprise one or more active agents. In one example, both the first and second plies 30, 32 comprise one or more active agents, which may be the same or different between the two plies 30, 32.

As described above, in certain examples, the article can be substantially formed from non-filament containing structures. In certain examples, the article can be entirely formed from non-filament containing structures. In such examples, the article can include one or more active agents releasable therefrom. Further, the article can be a multi-ply article including two or more plies, where surfaces of the two or more plies are substantially in contact with each other along either the length or width of the article. In certain examples, the article can include about 90% or more and/or about 92% or more and/or about 95% or more and/or about 97% or more and/or about 98% or more and/or about 99% or more and/or about 100% by weight of one or more active agents releasable therefrom when exposed to conditions of intended use, for example when exposed to conditions experienced in an automatic clothes dryer and/or in a washing machine. It will be appreciated that such articles can exhibit the consumer-preferred properties and possess the article dimensions in accordance with those described herein. In certain examples, the non-filament article can be substantially free of fluid.

With respect to an article including one or more fibrous elements, the fibrous elements and/or fibrous structures of the present invention are in solid form. However, the filament-forming composition used to make the fibrous elements of the present invention may be in the form of a liquid.

In one example, the fibrous structure comprises a plurality of identical or substantially identical from a compositional perspective of fibrous elements according to the present invention.

In another example, the fibrous structure may comprise two or more different fibrous elements according to the present invention. Non-limiting examples of differences in the fibrous elements may be physical differences such as differences in diameter, length, texture, shape, rigidness, elasticity, and the like; chemical differences such as cross-linking level, solubility, melting point, Tg, active agent, filament-forming material, color, level of active agent, basis weight, level of filament-forming material, presence of any coating on fibrous element, biodegradable or not, hydrophobic or not, contact angle, and the like; differences in whether the fibrous element loses its physical structure when the fibrous element is exposed to conditions of intended use; differences in whether the fibrous element's morphology changes when the fibrous element is exposed to conditions of intended use; and differences in rate at which the fibrous element releases one or more of its active agents when the fibrous element is exposed to conditions of intended use. In one example, two or more fibrous elements and/or particles within the fibrous structure may comprise different active agents. This may be the case where the different active agents may be incompatible with one another, for example an anionic surfactant (such as a shampoo active agent) and a cationic surfactant (such as a hair conditioner active agent).

In another example, the fibrous structure may exhibit different regions, such as different regions of basis weight, density and/or caliper. In yet another example, the fibrous structure may comprise texture on one or more of its surfaces. A surface of the fibrous structure may comprise a pattern, such as a non-random, repeating pattern. The fibrous structure may be embossed with an emboss pattern. In another example, the fibrous structure may comprise apertures. The apertures may be arranged in a non-random, repeating pattern.

In one example, the fibrous structure may comprise discrete regions of fibrous elements that differ from other parts of the fibrous structure.

The fibrous structure of the present invention may be used as is or may be coated with one or more active agents.

Particles

The particles may be water-soluble or water-insoluble. In one example, one group of particles may be water-soluble and a different group of particles may be water-insoluble. The particles, water-soluble or water-insoluble, may themselves deliver a benefit to the consumer. In another example, the particles, water-soluble or water-insoluble, may comprise one or more active agents (in other words, the particles may comprises active agent-containing particles). In still another example, the particles may consist essentially of and/or consist of one or more active agents (in other words, the particles, water-soluble and/or water-insoluble, may comprise 100% or greater than about 100% by weight on a dry particle basis of one or more active agents). In still another example, the particles may comprise water-soluble particles. In yet another example, the particles may comprise water-soluble, active agent-containing particles. In one other example, the water-insoluble particles comprise zeolites, porous zeolites, perfume-loaded zeolites, active loaded zeolites, silicas, perfume-loaded silicas, active loaded silicas, perfume microcapsules, clays, and mixtures thereof.

Fibrous Elements

The fibrous elements of the present invention are water-insoluble. In one example, the fibrous elements comprise one or more active agents that are releasable from the fibrous element, such as when the fibrous element and/or fibrous structure comprising the fibrous element is exposed to conditions of intended use. In addition to the one or more active agents, the fibrous elements may comprise one or more active agents.

In one example, the total level of the one or more active agents present in the fibrous elements and/or film structures and/or articles is 80% or greater and/or greater than 85% and/or greater than 90% and/or greater than 95% and/or greater than 96% and/or greater than 97% and/or greater than 98% and/or greater than 99% and/or about 100% by weight on a dry fibrous element and/or dry film structure and/or dry fibrous structure and/or dry article basis. In one example, one or more auxiliary ingredients, for example one or more filament-forming materials, such as one or more structurants, may be present in the fibrous elements and/or film structures and/or articles at a total level of 20% or less and/or less than 15% and/or less than 10% and/or less than 5% and/or less than 4% and/or less than 3% and/or less than 2% and/or less than 1% and/or about 0% by weight on a dry fibrous element and/or dry film structure and/or dry fibrous structure and/or dry article basis.

In one example, the fibrous element exhibits a diameter of less than 100 µm and/or less than 75 µm and/or less than 50 µm and/or less than 25 µm and/or less than 10 µm and/or less than 5 µm and/or less than 1 µm as measured according to the Diameter Test Method described herein. In another example, the fibrous element of the present invention exhibits a diameter of greater than 1 µm as measured according to the Diameter Test Method described herein. The diameter of a fibrous element of the present invention may be used to control the rate of release of one or more active agents present in the fibrous element and/or the rate of loss and/or altering of the fibrous element's physical structure.

The fibrous element may comprise two or more different active agents. In one example, the fibrous element comprises two or more different active agents, wherein the two or more different active agents are compatible with one another. In another example, the fibrous element comprises two or more different active agents, wherein the two or more different active agents are incompatible with one another.

In one example, the fibrous element may comprise an active agent within the fibrous element and an active agent on an external surface of the fibrous element, such as an active agent coating on the fibrous element. The active agent on the external surface of the fibrous element may be the same or different from the active agent present in the fibrous element. If different, the active agents may be compatible or incompatible with one another.

In another example, the fibrous structure or article of the present invention may comprise a coating on the external fibrous elements or filaments on one of the surfaces of the plies of the article. The coating may be applied to a surface of a ply and the surface with the coating may be an outer surface of the overall article or may be a surface internal to the article. Placement of the coating depends upon the benefit or active agent desired to be delivered. For example, coatings on an outer surface ply of the article would be more readily visible to a consumer, as it is on a consumer viewable surface. A coating on internal surface ply of the article may be less visible, as it may be hidden from direct view by a consumer. Placement of the coating on an internal surface and/or an outer surface of the article will be achieved as part of the article making process. A coating on an internal surface ply may be different or the same as coatings on the outer surface of the article. In one example, an article may have coatings on outer surfaces and/or internal surfaces of the article. In another example, an article may have coatings on outer surfaces and/or internal surfaces of plies making up the article. In yet another example, an article may have a silicone active agent comprising a coating or an aminosilicone comprising a coating on outer surfaces and/or internal surfaces of plies making up the article.

In one example, one or more active agents may be uniformly distributed or substantially uniformly distributed throughout the fibrous element. In another example, one or more active agents may be distributed as discrete regions within the fibrous element. In still another example, at least one active agent is distributed uniformly or substantially uniformly throughout the fibrous element and at least one other active agent is distributed as one or more discrete regions within the fibrous element. In still yet another example, at least one active agent is distributed as one or more discrete regions within the fibrous element and at least one other active agent is distributed as one or more discrete regions different from the first discrete regions within the fibrous element.

Active Agents

Non-limiting examples of suitable active agents for use in the fibrous elements and/or films and/or articles of the present invention include dryer added active agents, such as fabric conditioning active agents, and/or hair care conditioning active agents. As used herein a "fabric conditioning active agent" means any material that performs a function or delivers a benefit, such as modifying the physical or chemical properties of a treated material (e.g., fabric). Even though the description relates primarily to treating fabrics, the fabric conditioning active agents may also provide benefits, such as conditioning benefits to hair (e.g., hair conditioning active agents). Non-limiting examples of suitable fabric conditioning active agents and/or hair conditioning active agents include: perfumes, fabric conditioning agents, anti-static agents, crisping agents, water/stain repellents, stain release agents, refreshing agents, disinfecting agents, wrinkle resistance agents, wrinkle release agents, odor resistance agents, malodor control agents, abrasion resistance and protection agents, solvents, insect/pet repellents, wetting agents, UV protection agents, skin/fabric conditioning agents, skin/fabric nurturing agents, skin/fabric hydrating agents, color protection agents, dye fixatives, dye transfer inhibiting agents, silicones, preservatives and antimicrobials, fabric shrinkage-reducing agents, brighteners, hueing dyes, bleaches, chelants, antifoams, anti-scum agents, whitening agents, catalysts, cyclodextrin, zeolite, petrolatum, glycerin, triglycerides, vitamins, other skin care actives such as aloe vera, chamomile, shea butter and the like, mineral oils, and mixtures thereof. In one example, the articles of the present invention comprise one or more fabric conditioning active agents for imparting one or more fabric care benefits such as softening, anti-static, color protection, etc., to fabrics. In another example, the articles of the present invention may comprise one or more fabric conditioning active agents selected from the group consisting of: perfumes, builders, chelants, antioxidants, brighteners, sun fade inhibiting agents, UV absorbing agents, insect repellants, scents, bleaching agents, enzymes, antimicrobials, antibacterials, antifungals, perfume delivery systems, perfume microcapsules, dye transfer inhibiting agents, hueing dyes, soil release agents, such as soil release polymers, for example soil release polymer that comprise copolymeric blocks of terephthalate and polyethylene oxide or polypropylene oxide, and cationic soil release agents, colorants, preservatives, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, and mixtures thereof. In one example, the articles of the present invention comprise one or more hair conditioning active agents for imparting one or more hair care benefits such as softening, anti-static, color protection, etc. to hair. In another example, the articles of the present invention may comprise one or more active agents selected from the group consisting of: fabric care active agents, dishwashing active agents, carpet care active agents, surface care active agents, hair care active agents, air care active agents, oral care active agents, dryer added active agents, and mixtures thereof.

In one example, the articles of the present invention comprise one or more fabric conditioning active agents and/or hair conditioning active agents selected from the group consisting of: fatty fabric conditioning active agents (for example fatty acids and/or fatty acid derivatives and/or fatty alcohols), sulfonic acid derivatives, quaternary ammonium compounds, tertiary amines and salts thereof, nonionic surfactants, and mixtures thereof.

In one example, the fabric conditioning active agent and/or hair conditioning active agents comprises, alone or in combination with one or more fatty fabric conditioning active agents and/or fatty hair conditioning active agents (for example one or more fatty acids and/or one or more fatty alcohols), one or more quaternary ammonium compounds selected from the group consisting of: di(tallowyloxyethyl) hydroxyethylmethylammoniummethylsulfate, dimethyl bis(stearoyl oxyethyl)ammonium chloride, dimethyl bis(tallowyloxyethyl)ammonium chloride, dimethyl bis(tallowyloxyisopropyl)ammonium methylsulfate and mixtures thereof.

In one example, the fabric conditioning active agent and/or hair conditioning active agent comprises, alone or in combination with one or more quaternary ammonium compounds and/or one or more fatty alcohols, one or more fatty acids selected from the group consisting of: myristic acid, stearic acid, isostearic acid, cetearic acid, dodecanoic acid, linoleic acid, oleic acid, palmitic acid, lauric acid, and mixtures thereof.

In one example, the fabric conditioning active agent and/or hair conditioning active agent comprises, alone or in combination with one or more quaternary ammonium compounds and/or one or more fatty acids, one or more fatty alcohols selected from the group consisting of: cetyl alcohol, stearyl alcohol, behenyl alcohol, lauryl alcohol, myristic alcohol, isostearyl alcohol, arachidyl alcohol, and mixtures thereof.

Quaternary Ammonium Compounds

In one example, the fabric conditioning active agent and/or hair conditioning active agents comprises one or more fatty alcohols and one or more quaternary ammonium compounds. In one example, the article of the present invention comprises one or more fatty alcohols and one or more quaternary ammonium compounds in a weight ratio of greater than 1:1 and/or greater than 1.5:1 and/or greater than 1.75:1 and/or greater than 1.9:1.

In one example, the fabric conditioning active agent and/or hair conditioning active agent comprises one or more fatty acids and one or more quaternary ammonium compounds. In one example, the article of the present invention comprises one or more fatty acids and one or more quaternary ammonium compounds in a weight ratio of greater than 1:1 and/or greater than 1.5:1 and/or greater than 1.75:1 and/or greater than 1.9:1.

In one example, the fabric conditioning active agent and/or hair conditioning active agent comprises a quaternary ammonium compound. Non-limiting examples of quaternary ammonium compounds include alkylated quaternary ammonium compounds, ring or cyclic quaternary ammonium compounds, aromatic quaternary ammonium compounds, diquaternary ammonium compounds, alkoxylated quaternary ammonium compounds, amidoamine quaternary ammonium compounds, ester quaternary ammonium compounds, and mixtures thereof. See U.S. Patent Pub. 2005/0192207 at 57-66. The fabric conditioning active agents and/or hair conditioning active agents can be one or a mixture of a quaternary ammonium compound, a tertiary amine and or its salts, an ethoxylated fatty material, a fatty acid or a mixture thereof. Non-limiting examples of fabric conditioning active agents that are especially useful in the articles of the present invention are described in U.S. Pat. No. 4,103,047, Zaki et al., issued Jul. 25, 1978; U.S. Pat. No. 4,237,155, Kardouche, issued Dec. 2, 1980; U.S. Pat. No. 3,686,025, Morton, issued Aug. 22, 1972; U.S. Pat. No. 3,849,435, Diery et al., issued Nov. 19, 1974: and U.S. Pat. No. 4,073,996, Bedenk, issued Feb. 14, 1978; said patents are hereby incorporated herein by reference. Other fabric conditioning active agents and/or hair conditioning active agents are disclosed hereinafter.

Non-limiting examples of suitable quaternary ammonium compounds include cationic fabric conditioning active agents and/or cationic hair conditioning active agents and their salts such as dialkyl dimethylammonium chlorides, methylsulfates and ethylsulfates wherein the alkyl groups can be the same or different and contain from about 12 to about 22 carbon atoms. Non-limiting examples of such cationic fabric conditioning active agents and/or cationic hair conditioning active agents include ditallowalkyldimethylammonium methylsulfate (DTDMAMS), distearyldimethylammonium methylsulfate, dipalmityldimethylammonium methylsulfate and dibehenyldimethylammonium methylsulfate.

Another example of a suitable fabric conditioning active agent and/or hair conditioning active agents is an ester quaternary ammonium compound (EQA) selected from Formulas IA, IB, II, III, IV, and mixtures thereof.

Formula IA comprises:

$$[(R^1)_{4-p}-N^+-((CH_2)_v-Y-R^2)_p]X^-$$

wherein each Y=—O—(O)C—, or —C(O)—O—; p=1 to 3; each v=is an integer from 1 to 4, and mixtures thereof; each $R^1$ substituent is a short chain $C_1$-$C_6$, and/or $C_1$-$C_3$, alkyl group, e.g., methyl, ethyl, propyl, and the like, benzyl and mixtures thereof; each $R^2$ is a long chain, saturated and/or unsaturated (Iodine Value of from about 3 to about 60), $C_8$-$C_{30}$ hydrocarbyl, or substituted hydrocarbyl substituent and mixtures thereof; and the counterion, $X^-$, can be any softener-compatible anion, for example, methylsulfate, ethylsulfate, chloride, bromide, formate, sulfate, lactate, nitrate, benzoate, and the like, such as methylsulfate.

It will be understood that substituents $R^1$ and $R^2$ of Formula IA can optionally be substituted with various groups such as alkoxyl or hydroxyl groups. In one example, Formula IA compounds are diester quaternary ammonium salts (DEQA). At least about 25% of the DEQA is in the diester form, and from 0% to about 40% and/or less than about 30% and/or less than about 20%, can be EQA monoester (e.g., only one —Y—$R^2$ group).

Formula IB comprises:

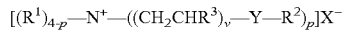

wherein each Y=—O—(O)C—, or —C(O)—O—; p=1 to 3; each v=is an integer from 1 to 4, and mixtures thereof; each $R^1$ substituent is a short chain $C_1$-$C_6$, and/or $C_1$-$C_3$, alkyl group, e.g., methyl, ethyl, propyl, and the like, benzyl and mixtures thereof; each $R^2$ is a long chain, saturated and/or unsaturated (Iodine Value of from about 3 to about 60), $C_8$-$C_{30}$ hydrocarbyl, or substituted hydrocarbyl substituent and mixtures thereof; each $R^3$ substituent is a short chain $C_1$-$C_6$ including benzyl, and/or $C_1$-$C_3$ alkyl group e.g., methyl, ethyl, propyl, and/or $C_1$-$C_2$ e.g., methyl, ethyl, and mixtures thereof; and the counterion, $X^-$, can be any softener-compatible anion, for example, methylsulfate, ethylsulfate, chloride, bromide, formate, sulfate, lactate, nitrate, benzoate, and the like, such as methylsulfate.

It will be understood that substituents $R^1$ and $R^2$ of Formula IB can optionally be substituted with various groups such as alkoxyl or hydroxyl groups. In one example, Formula IB compounds are diester quaternary ammonium salts (DEQA). At least about 25% of the DEQA is in the diester form, and from 0% to about 40% and/or less than about 30% and/or less than about 20%, can be EQA monoester (e.g., only one —Y—$R^2$ group).

As used herein, when the diester is specified, it will include the monoester that is normally present. For the optimal antistatic benefit the percentage of monoester should be as low as possible, such as less than about 2.5%. The level of monoester present can be controlled in the manufacturing of the EQA.

EQA compounds prepared with fully saturated acyl groups are excellent softeners. However, it has now been discovered that compounds prepared with at least partially unsaturated acyl groups have advantages (i.e., anti-static benefits) and are highly acceptable for consumer products when certain conditions are met. Variables that must be adjusted to obtain the benefits of using unsaturated acyl groups include the Iodine Value of the fatty acids, the odor of fatty acid starting material, and/or the EQA. Any reference to Iodine Value values hereinafter refers to Iodine Value of fatty acyl groups and not to the resulting EQA compound.

Some highly desirable, readily available sources of fatty acids such as tallow, possess odors that remain with the compound EQA despite the chemical and mechanical processing steps which convert the raw tallow to finished EQA. Such sources must be deodorized, e.g., by absorption, distillation (including stripping such as steam stripping), etc., as is well known in the art. In addition, care must be taken to minimize contact of the resulting fatty acyl groups to oxygen and/or bacteria by adding antioxidants, antibacterial agents, etc.

Generally, hydrogenation of fatty acids to reduce polyunsaturation and to lower Iodine Value to insure good color and odor stability leads to a high degree of trans configuration in the molecule. Therefore, diester compounds derived from fatty acyl groups having low Iodine Value values can be made by mixing fully hydrogenated fatty acid with touch hydrogenated fatty acid at a ratio which provides an Iodine Value of from about 3 to about 60. The polyunsaturation content of the touch hardened fatty acid should be less than about 5% and/or less than about 1%. During touch hardening the cis/trans isomer weight ratios are controlled by methods known in the art such as by optimal mixing, using specific catalysts, providing high $H_2$ availability, etc.

It has been found that a solvent may be used to facilitate processing of the Formula IA and/or IB EQA and/or of the fabric conditioning composition containing the EQA Formula IA and/or IB.

It has also been found that for good chemical stability of the diester quaternary compound in molten storage, water levels in the raw material must be minimized, for example to less than about 8% and/or less than about 5%. Storage temperatures should be kept as low as possible and still maintain a fluid material, ideally in the range of from about 45° C. to about 70° C. The optimum storage temperature for stability and fluidity depends on the specific Iodine Value of the fatty acid used to make the diester quaternary and the level/type of solvent selected. Also, exposure to oxygen should be minimized to keep the unsaturated groups from oxidizing. It can therefore be important to store the material under a reduced oxygen atmosphere such as a nitrogen blanket. It is important to provide good molten storage stability to provide a commercially feasible raw material that will not degrade noticeably in the normal transportation/storage/handling of the material in manufacturing operations.

The following are non-limiting examples of EQA Formula IA or IB (wherein all long-chain alkyl substituents are straight-chain):

Saturated

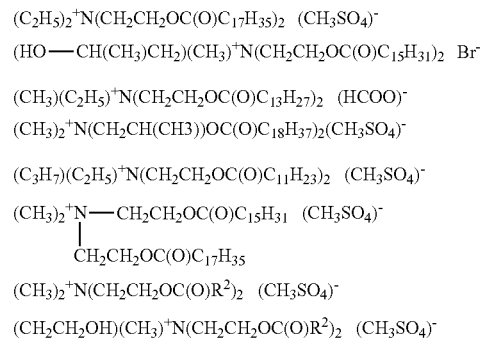

where —C(O)$R^2$ is derived from saturated tallow.

Unsaturated

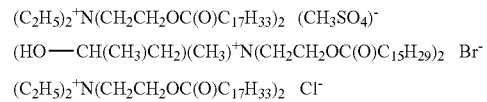

-continued $(CH_3)_2{}^+N(CH_2CH(CH_3))OC(O)C_{18}H_{35})_2(CH_3SO_4)^-$ $(CH_3)(C_2H_5)^+N(CH_2CH_2OC(O)C_{13}H_{27})_2$  $(C_6H_5COO)^-$

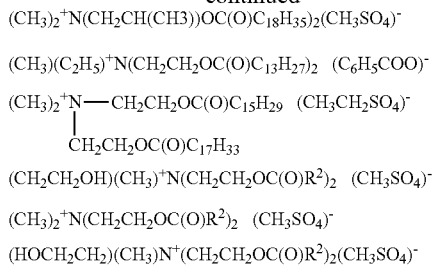

$(CH_2CH_2OH)(CH_3)^+N(CH_2CH_2OC(O)R^2)_2$  $(CH_3SO_4)^-$ $(CH_3)_2{}^+N(CH_2CH_2OC(O)R^2)_2$  $(CH_3SO_4)^-$ $(HOCH_2CH_2)(CH_3)N^+(CH_2CH_2OC(O)R^2)_2(CH_3SO_4)^-$ where —C(O)R² is derived from partially hydrogenated tallow or modified tallow having the characteristics set forth herein.

In addition to Formula IA and IB compounds, the compositions and articles of the present invention comprise EQA compounds of Formula II:

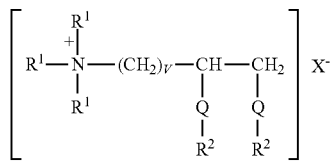

wherein, for any molecule: each Q is —O—C(O)— or —C(O)—O—; each $R^1$ is $C_1$-$C_4$ alkyl or hydroxy alkyl; $R^2$ and v are defined hereinbefore for Formula IA and IB; for example wherein $R^1$ is a methyl group, v is 1, Q is —O—C(O)—, each $R^2$ is $C_{14}$-$C_{18}$, and $X^-$ is methyl sulfate.

The straight or branched alkyl or alkenyl chains, $R^2$, have from about 8 to about 30 carbon atoms and/or from about 14 to about 18 carbon atoms and/or straight chains having from about 14 to about 18 carbon atoms.

Tallow is a convenient and inexpensive source of long chain alkyl and alkenyl materials.

A specific example of a Formula II EQA compound suitable for use as a fabric conditioning active agent and/or hair conditioning active agent herein is: 1,2-bis(tallowyl oxy)-3-trimethyl ammoniopropane methylsulfate (DTT-MAPMS).

Other examples of suitable Formula II EQA compounds of this invention are obtained by, e.g., replacing "tallowyl" in the above compounds with, for example, cocoyl, lauryl, oleyl, stearyl, palmityl, or the like; replacing "methyl" in the above compounds with ethyl, propyl, isopropyl, butyl, isobutyl, t-butyl, or the hydroxy substituted analogs of these radicals; and/or replacing "methylsulfate" in the above compounds with chloride, ethylsulfate, bromide, formate, sulfate, lactate, nitrate, and the like, for example methylsulfate.

In addition to Formula IA and IB and Formula II compounds, the articles of the present invention may comprise EQA compounds of Formula III:

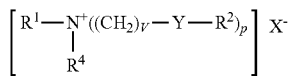

wherein $R^4$=a short chain $C_1$-$C_4$ alcohol; p is 2; $R^1$, $R^2$, v, Y, and $X^-$ are as previously defined for Formula IA and IB.

A specific example of a Formula III compound suitable for use as a fabric conditioning active agent and/or hair conditioning active agent herein is N-methyl-N,N-di-(2-($C_{14}$-$C_{18}$-acyloxy) ethyl), N-2-hydroxyethyl ammonium methylsulfate. An example of such as compound is N-methyl, N,N-di-(2-oleyloxyethyl)N-2-hydroxyethyl ammonium methylsulfate.

Fabric conditioning active agents and/or hair conditioning active agents of the present invention may also comprise Formula IV compounds:

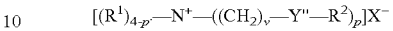

wherein $R^1$, $R^2$, p, v, and $X^-$ are previously defined in Formula IA and IB; and

and mixtures thereof, wherein at least one Y" group is

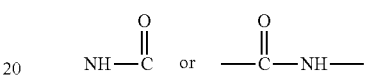

An example of this compound is methyl bis (oleyl amidoethyl) 2-hydroxyethyl ammonium methyl sulfate.

In one example, the fabric conditioning active agent and/or hair conditioning active agent of the present invention is a quaternary ammonium compound.

The compounds herein can be prepared by standard esterification and quaternization reactions, using readily available starting materials. General methods for preparation are disclosed in U.S. Pat. No. 4,137,180, which is incorporated herein by reference.

Tertiary Amines and Salts Thereof

Another fabric conditioning active agent and/or hair conditioning active agent useful in the fibrous elements and/or films and/or articles of the present invention is a carboxylic acid salt of a tertiary amine and/or ester amine having the formula:

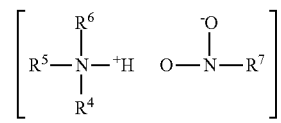

wherein $R^5$ is a long chain aliphatic group containing from about 8 to about 30 carbon atoms; $R^6$ and $R^4$ are the same or different from each other and are selected from the group consisting of aliphatic groups containing from about 1 to about 30 carbon atoms, hydroxyalkyl groups of the Formula $R^8OH$ wherein $R^8$ is an alkylene group of from about 2 to about 30 carbon atoms, and alkyl ether groups of the formula $R^9O(C_nH_{2n}O)_m$ wherein $R^9$ is alkyl and alkenyl of from about 1 to about 30 carbon atoms and hydrogen, n is 2 or 3, and m is from about 1 to about 30; wherein $R^4$, $R^5$, $R^6$, $R^8$, and $R^9$ chains can be ester interrupted groups; and wherein $R^7$ is selected from the group consisting of unsubstituted alkyl, alkenyl, aryl, alkaryl and aralkyl of about 8 to about 30 carbon atoms, and substituted alkyl, alkenyl, aryl, alkaryl, and aralkyl of from about 1 to about 30 carbon atoms wherein the substituents are selected from the group consisting of halogen, carboxyl, and hydroxyl, said composition having a thermal softening point of from about 35° C. to about 100° C.

The tertiary amine and/or ester amine can provide superior odor and/or improved fabric conditioning performance, compared to similar articles which utilize primary amine or ammonium compounds as the sole fabric conditioning active agent and/or hair conditioning active agent. Either $R^4$, $R^5$, $R^6$, $R^7$, $R^8$, and/or $R^9$ chains can contain unsaturation.

In one example, $R^5$ is an aliphatic chain containing from about 12 to about 30 carbon atoms, $R^6$ is an aliphatic chain of from about 1 to about 30 carbon atoms, and $R^4$ is an aliphatic chain of from about 1 to about 30 carbon atoms. In one example, suitable tertiary amines for static control performance are those containing unsaturation; e.g., oleyldimethylamine and/or soft tallowdimethylamine.

Examples of suitable tertiary amines as starting material for the reaction between the amine and carboxylic acid to form the tertiary amine salts are: lauryldimethylamine, myristyldimethyl-amine, stearyldimethylamine, tallowdimethylamine, coconutdimethylamine, dilaurylmethylamine, distearylmethylamine, ditallowmethylamine, oleyldimethylamine, dioleylmethylamine, lauryldi(3-hydroxypropyl)amine, stearyldi(2-hydroxyethyl)amine, trilaurylamine, laurylethylmethylamine, and

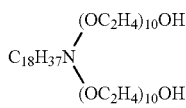

Non-limiting examples of suitable fatty acids are those wherein $R^7$ is a long chain, unsubstituted alkyl or alkenyl group of from about 8 to about 30 carbon atoms and/or from about 11 to about 17 carbon atoms.

Examples of specific carboxylic acids as a starting material are: formic acid, acetic acid, lauric acid, myristic acid, palmitic acid, stearic acid, oleic acid, oxalic acid, adipic acid, 12-hydroxy stearic acid, benzoic acid, 4-hydroxy benzoic acid, 3-chloro benzoic acid, 4-nitro benzoic acid, 4-ethyl benzoic acid, 4-(2-chloroethyl)benzoic acid, phenylacetic acid, (4-chlorophenyl)acetic acid, (4-hydroxyphenyl) acetic acid, and phthalic acid.

Non-limiting examples of suitable carboxylic acids are stearic, oleic, lauric, myristic, palmitic, and mixtures thereof.

The amine salt can be formed by a simple addition reaction, well known in the art and disclosed in U.S. Pat. No. 4,237,155, Kardouche, issued Dec. 2, 1980, which is incorporated herein by reference. Excessive levels of free amines may result in odor problems, and generally free amines provide poorer softening performance than the amine salts.

Non-limiting examples of amine salts for use herein are those wherein the amine moiety is a $C_8$-$C_{30}$ alkyl or alkenyl dimethyl amine and/or a di-$C_8$-$C_{30}$ alkyl or alkenyl methyl amine, and the acid moiety is a $C_8$-$C_{30}$ alkyl and/or alkenyl monocarboxylic acid. The amine and the acid, respectively, used to form the amine salt will often be of mixed chain lengths rather than single chain lengths, since these materials are normally derived from natural fats and oils, or synthetic processed which produce a mixture of chain lengths. Also, it is often desirable to utilize mixtures of different chain lengths in order to modify the physical or performance characteristics of the softening composition.

Specific examples of amine salts for use in the present invention are oleyldimethylamine stearate, stearyldimethylamine stearate, stearyldimethylamine myristate, stearyldimethylamine oleate, stearyldimethylamine palmitate, distearylmethylamine palmitate, distearylmethylamine laurate, and mixtures thereof. In one example, a mixture of amine salts is oleyldimethylamine stearate and distearylmethylamine myristate, in a ratio of 1:10 to 10:1 and/or about 1:1.

Sulfonic Acid Fatty Amine Salts

Other fatty amine salts can be used in the present invention. These salts are similar to those previously described but replacing the carboxylic acid with a sulfonic acid derivative. The amine salt can be formed by a simple addition reaction, well known in the art and disclosed in U.S. Pat. No. 4,861,502, Caswell issued Aug. 29, 1989, which is incorporated herein by reference. Such sulfonic acid derivates include but not limited to methylsulfonic acid, benzenesulfonic acid, toluensulfonic acid, cumenesulfonic and mixtures thereof.

Nonionic Fabric Conditioning Active Agents and/or Hair Conditioning Active Agents Non-limiting examples of suitable nonionic fabric conditioning active agents and/or nonionic hair conditioning active agents for use in the fibrous elements and/or films and/or articles of the present invention have an HLB of from about 2 to about 9, and more typically from about 3 to about 7. In general, the materials selected should be relatively crystalline and higher melting, (e.g., >25° C.).

The level of optional nonionic fabric conditioning active agents and/or optional nonionic hair conditioning active agents in the article is typically from about 0.1% to about 50% and/or from about 5% to about 30%.

Non-limiting examples of suitable nonionic fabric conditioning active agents and/or nonionic hair conditioning active agents are fatty acid partial esters of polyhydric alcohols, or anhydrides thereof, wherein the alcohol or anhydride contains from about 2 to about 18 and/or from about 2 to about 8 carbon atoms, and each fatty acid moiety contains from about 8 to about 30 and/or from about 12 to about 20 carbon atoms. Typically, such nonionic fabric conditioning active agents and/or hair conditioning active agents contain from about one to about 3 and/or about 2 fatty acid groups per molecule.

The polyhydric alcohol portion of the ester can be ethylene glycol, glycerol, poly (e.g., di-tri-, tetra, penta-, and/or hexa-) glycerol, xylitol, sucrose, erythritol, pentaerythritol, sorbitol or sorbitan.

The fatty acid portion of the ester is normally derived from fatty acids having from about 8 to about 30 and/or from about 12 to about 22 carbon atoms. Typical examples of said fatty acids being lauric acid, myristic acid, palmitic acid, stearic acid, oleic acid, and behenic acid.

Non-limiting example of suitable nonionic fabric conditioning active agents and/or hair conditioning active agents for use in the present invention are $C_{10}$-$C_{26}$ acyl sorbitan esters and polyglycerol monostearate. Sorbitan esters are esterified dehydration products of sorbitol. The sorbitan ester may comprise a member selected from the group consisting of $C_{10}$-$C_{26}$ acyl sorbitan monoesters and/or $C_{10}$-$C_{26}$ acyl sorbitan diesters and/or ethoxylates of said esters wherein one or more of the unesterified hydroxyl groups in said esters contains from about 1 to about 6 oxyethylene units, and mixtures thereof. For the purpose of the present invention, sorbitan esters containing unsaturation (e.g., sorbitan monooleate) can be utilized.

Sorbitol, which is typically prepared by the catalytic hydrogenation of glucose, can be dehydrated in well-known fashion to form mixtures of 1,4- and 1,5-sorbitol anhydrides and small amounts of isosorbides. (See U.S. Pat. No. 2,322,821, Brown, issued Jun. 29, 1943, incorporated herein by reference.)

The foregoing types of complex mixtures of anhydrides of sorbitol are collectively referred to herein as "sorbitan." It will be recognized that this "sorbitan" mixture will also contain some free, uncyclized sorbitol.

In one example, the sorbitan fabric conditioning active agents and/or hair conditioning active agents of the type employed herein can be prepared by esterifying the "sorbitan" mixture with a fatty acyl group in standard fashion, e.g., by reaction with a fatty acid halide, fatty acid ester, and/or fatty acid. The esterification reaction can occur at any of the available hydroxyl groups, and various mono-, di-, etc., esters can be prepared. In fact, mixtures of mono-, di-, tri-, etc., esters almost always result from such reactions, and the stoichiometric ratios of the reactants can be simply adjusted to favor the desired reaction product.

For commercial production of the sorbitan ester materials, etherification and esterification are generally accomplished in the same processing step by reacting sorbitol directly with fatty acids. Such a method of sorbitan ester preparation is described more fully in MacDonald, "Emulsifiers: Processing and Quality Control", *Journal of the American Oil Chemists' Society*, Vol. 45, October 1968. Details, including formula, of the examples of sorbitan esters can be found in U.S. Pat. No. 4,128,484, incorporated hereinbefore by reference.

Certain derivatives of the sorbitan esters herein, especially the "lower" ethoxylates thereof (i.e., mono-, di-, and tri-esters wherein one or more of the unesterified —OH groups contain one to about twenty oxyethylene moieties (Tweens®) are also useful in the articles of the present invention. Therefore, the term "sorbitan ester" is intended to include such derivatives.

For the purposes of the present invention, in one example, a significant amount of di- and tri-sorbitan esters are present in the ester mixture. In another example, an ester mixture may have from about 20-50% mono-ester, about 25-50% di-ester and about 10-35% of tri- and tetra-esters. Material which is sold commercially as sorbitan mono-ester (e.g., monostearate) typically contains significant amounts of di- and tri-esters. A typical analysis of commercial sorbitan monostearate indicates that it comprises about 27% mono-, about 32% di- and about 30% tri- and tetra-esters. Mixtures of sorbitan stearate and sorbitan palmitate having stearate/palmitate weight ratios varying between 10:1 and 1:10, and 1,5-sorbitan esters are also useful. In addition, both the 1,4- and 1,5-sorbitan esters are useful herein.

Other useful alkyl sorbitan esters for use as fabric conditioning active agents and/or hair conditioning active agents herein include sorbitan monolaurate, sorbitan monomyristate, sorbitan monopalmitate, sorbitan monobehenate, sorbitan monooleate, sorbitan dilaurate, sorbitan dimyristate, sorbitan dipalmitate, sorbitan distearate, sorbitan dibehenate, sorbitan dioleate, and mixtures thereof, and mixed tallowalkyl sorbitan mono- and di-esters. Such mixtures are readily prepared by reacting the foregoing hydroxy-substituted sorbitans, particularly the 1,4- and 1,5-sorbitans, with the corresponding acid, ester, or acid chloride in a simple esterification reaction. It is to be recognized, of course, that commercial materials prepared in this manner will comprise mixtures usually containing minor proportions of uncyclized sorbitol, fatty acids, polymers, isosorbide structures, and the like. In the present invention, it is desirable to keep such impurities present at as low a level as practical.

The sorbitan esters employed herein may contain up to about 15% by weight of esters of the $C_{20}$-$C_{26}$, and higher, fatty acids, as well as minor amounts of $C_8$, and lower, fatty esters.

Glycerol and polyglycerol esters, especially glycerol, diglycerol, triglycerol, and polyglycerol mono- and/or di-esters, in one example mono- (e.g., polyglycerol monostearate with a trade name of Radiasurf 7248). Glycerol esters can be prepared from naturally occurring triglycerides by normal extraction, purification and/or interesterification processes or by esterification processes of the type set forth hereinbefore for sorbitan esters. Partial esters of glycerin can also be ethoxylated to form usable derivatives that are included within the term "glycerol esters."

Useful glycerol and polyglycerol esters include monoesters with stearic, oleic, palmitic, lauric, isostearic, myristic, and/or behenic acids and the diesters of stearic, oleic, palmitic, lauric, isostearic, behenic, and/or myristic acids. It is understood that the typical mono-ester contains some di- and tri-ester, etc.

The "glycerol esters" also include the polyglycerol, e.g., diglycerol through octaglycerol esters. The polyglycerol polyols are formed by condensing glycerin or epichlorohydrin together to link the glycerol moieties via ether linkages. The mono- and/or diesters of the polyglycerol polyols may be used, the fatty acyl groups typically being those described hereinbefore for the sorbitan and glycerol esters.

Fatty Fabric Conditioning Active Agents and/or Hair Conditioning Active Agents

The fibrous elements and/or films and/or articles of the present invention further comprise one or more fatty fabric conditioning active agents and/or fatty hair conditioning active agents, for example one or more high melting point fatty compounds. The high melting point fatty compound can be included in the composition at a level of from about 10 wt % to about 85 wt % and/or from 20 wt % to 70 wt % and/or from about 50 wt % to about 70 wt % and/or from about 10 wt % to about 20 wt % of the fibrous element and/or film and/or article. In one example, the fatty fabric conditioning active agent and/or fatty hair conditioning active agent is selected from the group consisting of: fatty amphiphiles, fatty alcohols, fatty acids, fatty amides, fatty esters and mixtures thereof.

In one example, the fatty fabric conditioning active agents and/or fatty hair conditioning active agents have a melting point of 25° C. or higher and/or 40° C. or higher and/or 45° C. or higher and/or 50° C. or higher and/or to about 90° C. and/or to about 80° C. and/or to about 70° C. and/or to about 65° C. and are considered as high melting point fatty fabric conditioning active agents and/or high melting point fatty hair conditioning active agents. The fatty fabric conditioning active agent and/or fatty hair conditioning active agent may be used as a single compound or as a blend or mixture of at least two fatty fabric conditioning active agents and/or a mixture of at least two fatty hair conditioning active agents. When used as such blend or mixture, the above melting point means the melting point of the blend or mixture.

The fatty fabric conditioning active agents and/or fatty hair conditioning active agents useful herein may be selected from the group consisting of fatty alcohols, fatty acids, fatty alcohol derivatives, fatty acid derivatives, and mixtures thereof. It is understood by the artisan that the fatty fabric conditioning active agents and/or fatty hair conditioning active agents disclosed herein may in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain fatty fabric conditioning active agents and/or fatty hair conditioning active agents having certain required carbon atoms may have a melting point of less than the above. Such fatty fabric conditioning active agents and/or fatty hair conditioning active agents of low melting point (a melting point less than 25° C. and/or less than 20° C.) are not intended to be included in this section. Non-limiting examples of the high melting point fatty fabric conditioning active agents and/or high melting point fatty hair conditioning active agents are found in International Cosmetic Ingredient Dictionary, Fifth Edition, 1993, and CTFA Cosmetic Ingredient Handbook, Second Edition, 1992.

Fatty Acids

The fabric conditioning active agents and/or hair conditioning active agents in the articles of the present invention may further comprise one or more fatty acids. Typically, the fatty acid is present to improve the processability of the composition, and is admixed with any material, or materials, that are difficult to process, especially as a result of having a high viscosity. The fatty acid provides improved viscosity and/or processability, without harming softening or antistatic performance of the article.

Non-limiting examples of suitable fatty acids are those containing a long chain, unsubstituted alkenyl group of from about 8 to about 30 carbon atoms and/or from about 11 to about 18 carbon atoms. Examples of specific carboxylic acids are: oleic acid, linoleic acid, and mixtures thereof. Although unsaturated fatty acids are desirable, the unsaturated fatty acids can also be used in combination with saturated fatty acids like stearic, palmitic, and/or lauric acids. Non-limiting examples of suitable carboxylic acids are oleic, linoleic, tallow fatty acids, and mixtures thereof.

In one example, the fatty acid is added to the quaternization reaction mixture used to form the biodegradable quaternary ammonium compounds of Formulas II, III, and/or IV as described hereinbefore to lower the viscosity of the reaction mixture to less than about 1500 cps and/or less than about 1000 cps and/or less than about 800 cps. The solvent level of added fatty acid may be from about 5% to about 30% and/or from about 10% to about 25% and/or from about 10% to about 20%. The unsaturated fatty acid can be added before the start of the quaternization reaction and/or may be added during the quaternization reaction when it is needed to reduce the viscosity which increases with increased level of quaternization. In one example, the addition occurs when at least about 60% of the product is quaternized. This allows for a low viscosity for processing while minimizing side reactions that can occur when the quaternizing agent reacts with the fatty acid. The quaternization reactions are well known and include, e.g., with respect to Formula IA and/or IB compounds, those processes described in U.S. Pat. No. 3,915,867, Kang et al., issued Oct. 28, 1975; U.S. Pat. No. 4,830,771, Ruback et al., issued May 16, 1989; and U.S. Pat. No. 5,296,622, Uphues et al., issued Mar. 22, 1994, all of said patents being incorporated herein by reference. The resulting quaternized biodegradable fabric conditioning active agents can be used without removal of the unsaturated fatty acid, and, in fact, are more useful since the mixture is more fluid and more easily handled.

Another example of a type of fabric conditioning active agents and/or hair conditioning active agents is described in detail in U.S. Pat. No. 4,661,269, Toan Trinh, Errol H. Wahl, Donald M. Swartley and Ronald L. Hemingway, issued Apr. 28, 1987, said patent being incorporated herein by reference Fatty Alcohols Non-limiting examples of suitable fatty alcohols useful as fatty fabric conditioning active agents and/or fatty hair conditioning active agents are those fatty alcohols having from about 14 to about 30 carbon atoms and/or from about 16 to about 22 carbon atoms. These fatty alcohols are saturated and can be straight or branched chain alcohols.

Suitable fatty alcohols include, but are not limited to, cetyl alcohol (having a melting point of about 56° C.), stearyl alcohol (having a melting point of about 58-59° C.), behenyl alcohol (having a melting point of about 71° C.), and mixtures thereof. These fatty alcohols are known to have the above referenced melting points, however, they often have lower melting points when supplied, since such supplied products are often mixtures of fatty alcohols having alkyl chain length distributions in which the main alkyl chain is cetyl, stearyl or behenyl group. Generally, in the mixture, the weight ratio of cetyl alcohol to stearyl alcohol can be from about 1:9 to 9:1 and/or from about 1:4 to about 4:1 and/or from about 1:2.3 to about 1.5:1.

Dispersing Agents

In one example, the fabric conditioning active agents and/or hair conditioning active agents may comprise a dispersing agent. The dispersing agent, when present, greatly increases the wetting, hydration, and dispersion of the fabric conditioning active agents and/or hair conditioning active agents. The dispersing agent can be included at a level of from about 1 wt % to about 30 wt % of the composition, alternatively from about 5 wt % to about 15 wt %, and alternatively from about 5 wt % to about 10 wt %. A surfactant from the nonionic class of alkyl glucamides can improve the wetting and hydration when added to the solid conditioner formula. The alkyl glucamide surfactant contains a hydrophobic tail of about 8-18 carbons and a nonionic head group of glucamide. For glucamide, the presence of the amide and hydroxyl groups may provide sufficient polarity that balances the hydrophobic carbon tail in such a way to permit the surfactant's solubility in the conditioner oils and also imparts a rapid dispersion of the conditioner ingredients upon exposure to water. Other similar dispersing agents include, but are not limited to, reverse alkyl glucamides, cocoamiodpropyl betaines, alkyl glucoside, Triethanol amine, cocamide MEAs and mixtures thereof.

Cationic Surfactants

The fabric conditioning active agent and/or hair conditioning active agent of the present invention may comprise a cationic surfactant. When present, the cationic surfactant may be present at a level of from about 1 wt % to about 60 wt %, alternatively from about 10 wt % to about 50 wt %, alternatively from about 20 wt % to about 40 wt % of the article.

Cationic surfactants useful herein can be one cationic surfactant or a mixture of two or more cationic surfactants. The cationic surfactant can be selected from the group consisting of, but not limited to: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt, a tertiary amine and combinations thereof.

Mono-Long Alkyl Amines

Mono-long alkyl amine useful herein are those having one long alkyl chain of from 12 to 30 carbon atoms, alternatively from 16 to 24 carbon atoms, alternatively from 18 to 22 alkyl group. Mono-long alkyl amines useful herein also include mono-long alkyl amidoamines. Primary, secondary, and tertiary fatty amines are useful.

Suitable for use in the articles of the present invention are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines can be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; alternatively l-glutamic acid, lactic acid, citric acid, at a molar ratio of the amine to the acid of from about 1:0.3 to about 1:2, alternatively from about 1:0.4 to about 1:1.

Mono-Long Alkyl Quaternized Ammonium Salts

The mono-long alkyl quaternized ammonium salts useful herein are those having one long alkyl chain which has from 12 to 30 carbon atoms, alternatively from 16 to 24 carbon atoms, alternatively a C18-22 alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the following formula (V):

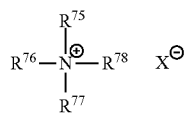

(V)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. One of $R^{75}$, $R^{76}$, $R^{77}$ and $R^{78}$ can be selected from an alkyl group of from 12 to 30 carbon atoms, alternatively from 16 to 24 carbon atoms, alternatively from 18 to 22 carbon atoms, alternatively 22 carbon atoms; the remainder of $R^{75}$, $R^{76}$, $R^{77}$ and $R^{78}$ can be independently selected from $CH_3$, $C_2H_5$, $C_2H_4OH$, and mixtures thereof; and X can be selected from the group consisting of Cl, Br, $CH_3OSO_3$, $C_2H_5OSO_3$, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts can be combined with a mono-long alkyl quaternized ammonium salt and/or mono-long alkyl amine salt, at the weight ratio of from 1:1 to 1:5, alternatively from 1:1.2 to 1:5, alternatively from 1:1.5 to 1:4, in view of stability in rheology and conditioning benefits.

Di-long alkyl quaternized ammonium salts useful herein are those having two long alkyl chains of from 12 to 30 carbon atoms, alternatively from 16 to 24 carbon atoms, alternatively from 18 to 22 carbon atoms. Such di-long alkyl quaternized ammonium salts useful herein are those having the formula (VI):

(VI)

wherein two of $R^{71}$, $R^{72}$, $R^{73}$ and $R^{74}$ are selected from an aliphatic group of from 12 to 30 carbon atoms, alternatively from 16 to 24 carbon atoms, alternatively from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, alternatively from 1 to 3 carbon atoms or an aromatic, alkoxy, polyoxyalkylene, alkylamido, hydroxyalkyl, aryl or alkylaryl group having up to about 8 carbon atoms; and $X^-$ is a salt-forming anion selected from the group consisting of halides such as chloride and bromide, C1-C4 alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Two of $R^{71}$, $R^{72}$, $R^{73}$ and $R^{74}$ can be selected from an alkyl group of from 12 to 30 carbon atoms, alternatively from 16 to 24 carbon atoms, alternatively from 18 to 22 carbon atoms; and the remainder of $R^{71}$, $R^{72}$, $R^{73}$ and $R^{74}$ are independently selected from $CH_3$, $C_2H_5$, $C_2H_4OH$, $CH_2C_6H_5$, and mixtures thereof.

Suitable di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

Optional Ingredients

In addition to the one or more fabric conditioning active agents and/or hair conditioning active agents described above, the articles of the present invention may further comprise one or more optional ingredients. When present, the one or more optional ingredients may be present in and/or on the article at a level of from about 0.01% to about 10% and/or from about 0.1% to about 5% and/or from about 0.1% to about 2% by weight of the article. Non-limiting examples of such optional ingredient include soil release agents, such as soil release polymers, for example soil release polymer that comprise copolymeric blocks of terephthalate and polyethylene oxide or polypropylene oxide, and cationic soil release agents, anti-oxidants, colorants, preservatives, optical brighteners, opacifiers, stabilizers such as guar gum and polyethylene glycol, anti-shrinkage agents, anti-wrinkle agents, soil release agents, fabric crisping agents, reductive agents, spotting agents, germicides, fungicides, anti-corrosion agents, antifoam agents, deterrent agents, such as bittering agents, and the like.

Non-limiting examples of suitable deterrent agents are found in U.S. Patent Application Publication No. US 2016-0258083 A1.

Auxiliary Ingredients

In addition to the one or more active agents, the articles of the present invention may further comprise one or more auxiliary ingredients, for example one or more structurants.

Non-limiting examples of suitable auxiliary ingredients, for example structurants, are selected from the group consisting of: polymeric structurants, inorganic structurants, and mixtures thereof. In one example, the auxiliary ingredient, for example structurant, comprises a polymeric structurant selected from the group consisting of: polyvinylpyrrolidone, copolymers of vinylpyrrolidone, polydimethylacrylamide, copolymers of dimethylacrylamide, and mixtures thereof. In one example, the structurant comprises polyvinylpyrrolidone. In one example, the structurant comprises polydimethylacrylamide. In one example, the structurant comprises an inorganic structurant selected from the group consisting of clays, silica, and mixtures thereof.

The one or more auxiliary ingredients, for example one or more structurants, when present, may be dispersed throughout, for example homogeneously, the one or more active agents within the filament-forming composition and/or fibrous element and/or fibrous structure and/or film structure and/or article.

When present, the one or more auxiliary ingredients may be present in the filament-forming composition and/or fibrous element and/or fibrous structure and/or film structure and/or article at a total level of less than 20% or less and/or less than 15% and/or less than 10% and/or less than 5% and/or less than 4% and/or less than 3% and/or less than 2% and/or less than 1% and/or about 0% by weight on a dry filament-forming composition and/or a dry fibrous element and/or dry film structure and/or dry fibrous structure and/or dry article basis.

Method for Making Filament-Forming Composition

The filament-forming composition of the present invention may be made by any suitable process so long as the filament-forming composition is suitable for making the article of the present invention.

In one example, one or more active agents, for example one or more fabric conditioning active agents and/or hair conditioning active agents, are added (in the absence of free water) to a metal beaker and heated to a temperature sufficient to melt the active agents, for example 80° C. The active agents are melted and optionally agitated until they form a homogeneous fluid.

After melting the active agents, one or more auxiliary ingredients, for example one or more filament-forming materials, such as one or more structurants, may be added to the homogeneous fluid of active agents. The auxiliary ingredients, when added, are stirred into the homogeneous fluid of active agents until the auxiliary ingredients are dispersed, for example homogeneously dispersed, throughout the homogeneous fluid of active agents and/or are homogeneously dissolved within the homogeneous fluid of active agents. This all occurs while maintaining the homogeneous fluid of active agents at a temperature of at least the melting point of the lowest melting point active agent, for example 80° C.

The filament-forming composition may then be used to make fibrous elements and/or fibrous structures and/or film structures and/or articles of the present invention.

Method for Making Fibrous Elements

The fibrous elements of the present invention may be made by any suitable process. A non-limiting example of a suitable process for making the fibrous elements is described below.

Figure 14:
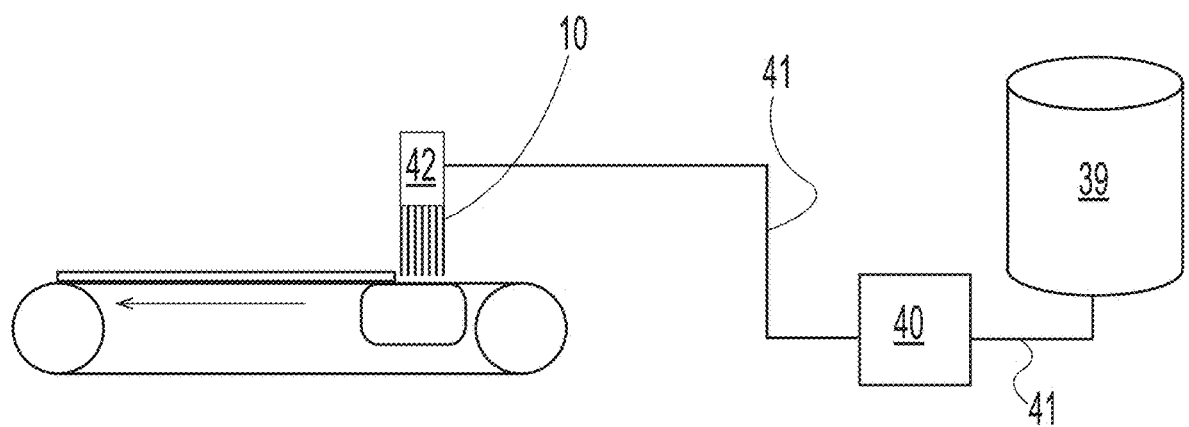
FIG. 14 is a schematic representation of an example of a process for making an example of a fibrous structure according to the present disclosure.
Figure 15:
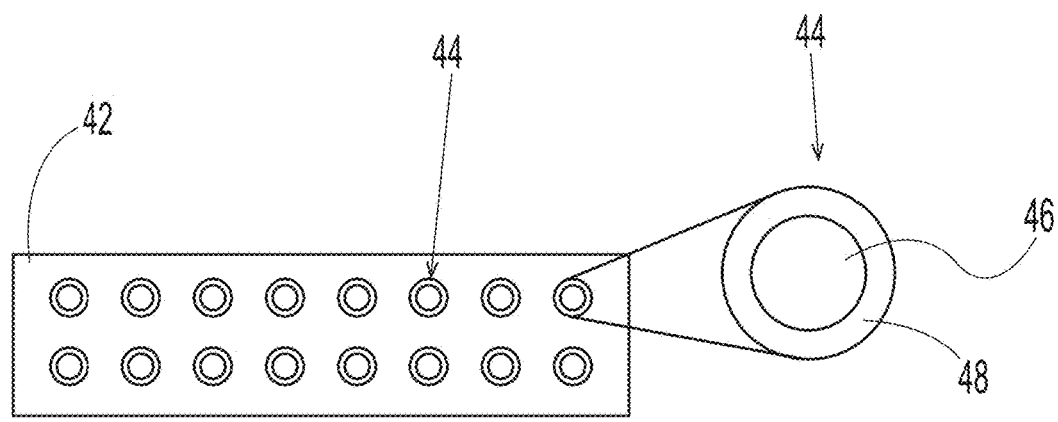
FIG. 15 is a schematic representation of an example of a die with a magnified view used in the process of FIG. 14.

As shown in FIGS. 14 and 15, the fibrous elements of the present invention may be made as follows. Fibrous elements may be formed by means of a small-scale apparatus, a schematic representation of which is shown in FIGS. 14 and 15. A pressurized tank 39, suitable for batch operation is filled with a suitable filament-forming composition according to the present invention. A pump 40 such as a Zenith®, type PEP II, having a capacity of 5.0 cubic centimeters per revolution ($cm^3$/rev), manufactured by Parker Hannifin Corporation, Zenith Pumps division, of Sanford, N.C., USA may be used to facilitate transport of the filament-forming composition via pipes 41 to a spinning die 42. The flow of the filament-forming composition from the pressurized tank 39 to the spinning die 42 may be controlled by adjusting the number of revolutions per minute (rpm) of the pump 40. Pipes 41 are used to connect the pressurized tank 39, the pump 40, and the spinning die 42.

The spinning die 42 shown in FIG. 14 has several rows of circular extrusion nozzles (fibrous element-forming holes 44) spaced from one another at a pitch P of about 1.524 millimeters (about 0.060 inches). The nozzles have individual inner diameters of about 0.305 millimeters (about 0.012 inches) and individual outside diameters of about 0.813 millimeters (about 0.032 inches). Each individual nozzle is encircled by an annular and divergently flared orifice (concentric attenuation fluid hole 48 to supply attenuation air to each individual melt capillary 46. The filament-forming composition extruded through the nozzles is surrounded and attenuated by generally cylindrical, humidified air streams supplied through the orifices.

In one example, as shown in FIGS. 14 and 15, a method for making a fibrous element 10 according to the present invention comprises the steps of:

a. providing a filament-forming composition comprising one or more filament-forming materials, and optionally one or more active agents; and b. spinning the filament-forming composition, such as via a spinning die 42, into one or more fibrous elements, such as filaments 10, comprising the one or more filament-forming materials and optionally, the one or more active agents. The one or more active agents may be releasable from the fibrous element when exposed to conditions of intended use. The total level of the one or more filament-forming materials present in the fibrous element, for example filament 10, when active agents are present therein, may be less than 80% and/or less than 70% and/or less than 65% and/or 50% or less by weight on a dry fibrous element basis and/or dry fibrous structure basis and the total level of the one or more active agents, when present in the fibrous element may be greater than 20% and/or greater than 35% and/or 50% or greater 65% or greater and/or 80% or greater by weight on a dry fibrous element basis and/or dry fibrous structure basis.

As shown in FIG. 15, the spinning die 42 may comprise a plurality of fibrous element-forming holes 44 that include a melt capillary 46 encircled by a concentric attenuation fluid hole 48 through which a fluid, such as air, passes to facilitate attenuation of the filament-forming composition into a fibrous element, for example a filament 10 as it exits the fibrous element-forming hole 44.

Attenuation air can be provided by heating compressed air from a source by an electrical-resistance heater, for example, a heater manufactured by Chromalox, Division of Emerson Electric, of Pittsburgh, Pa., USA. An appropriate quantity of steam was added to saturate or nearly saturate the heated air at the conditions in the electrically heated, thermostatically controlled delivery pipe. Condensate is removed in an electrically heated, thermostatically controlled, separator.

The embryonic fibrous elements are dried by a drying air stream having a temperature from about 149° C. (about 300° F.) to about 315° C. (about 600° F.) by an electrical resistance heater (not shown) supplied through drying nozzles and discharged at an angle of about 90° relative to the general orientation of the embryonic fibrous elements being extruded. The dried embryonic fibrous elements are collected on a collection device, such as, for example, a movable foraminous belt or patterned collection belt. The addition of a vacuum source directly under the formation zone may be used to aid collection of the fibers.

In one example, during the spinning step, any volatile solvent, such as water, present in the filament-forming composition is removed, such as by drying, as the fibrous element 10 is formed. In one example, greater than 30% and/or greater than 40% and/or greater than 50% of the weight of the filament-forming composition's volatile solvent, such as water, is removed during the spinning step, such as by drying the fibrous element being produced.

The filament-forming composition may comprise any suitable total level of filament-forming materials and any suitable level of active agents so long as the fibrous element produced from the filament-forming composition comprises a total level of filament-forming materials in the fibrous element of from about 5% to 50% or less by weight on a dry fibrous element basis and/or dry particle basis and/or dry fibrous structure basis and a total level of active agents in the fibrous element of from 50% to about 95% by weight on a dry fibrous element basis and/or dry particle basis and/or dry fibrous structure basis.

In one example, the filament-forming composition may comprise any suitable total level of filament-forming materials and any suitable level of active agents so long as the fibrous element produced from the filament-forming composition comprises a total level of filament-forming materials in the fibrous element and/or particle of from about 5% to 50% or less by weight on a dry fibrous element basis and/or dry particle basis and/or dry fibrous structure basis and a total level of active agents in the fibrous element and/or particle of from 50% to about 95% by weight on a dry fibrous element basis and/or dry particle basis and/or dry fibrous structure basis, wherein the weight ratio of filament-forming material to total level of active agents is 1 or less.

In one example, the filament-forming composition comprises from about 1% and/or from about 5% and/or from about 10% to about 50% and/or to about 40% and/or to about 30% and/or to about 20% by weight of the filament-forming composition of filament-forming materials; from about 1% and/or from about 5% and/or from about 10% to about 50% and/or to about 40% and/or to about 30% and/or to about 20% by weight of the filament-forming composition of active agents; and from about 20% and/or from about 25% and/or from about 30% and/or from about 40% and/or to about 80% and/or to about 70% and/or to about 60% and/or to about 50% by weight of the filament-forming composition of a volatile solvent, such as water. The filament-forming composition may comprise minor amounts of other active agents, such as less than 10% and/or less than 5% and/or less than 3% and/or less than 1% by weight of the filament-forming composition of plasticizers, pH adjusting agents, and other active agents.

The filament-forming composition is spun into one or more fibrous elements and/or particles by any suitable spinning process, such as meltblowing, spunbonding, electro-spinning, and/or rotary spinning. In one example, the filament-forming composition is spun into a plurality of fibrous elements and/or particles by meltblowing. For example, the filament-forming composition may be pumped from a tank to a meltblown spinnerette. Upon exiting one or more of the filament-forming holes in the spinnerette, the filament-forming composition is attenuated with air to create one or more fibrous elements and/or particles. The fibrous elements and/or particles may then be dried to remove any remaining solvent used for spinning, such as the water.

The fibrous elements and/or particles of the present invention may be collected on a belt, such as a patterned belt to form a fibrous structure comprising the fibrous elements and/or particles.

Method for Making Article

In one example, the filament-forming composition of the present invention may be made by the following steps:
a. subjecting one or more active agents to a temperature sufficient to melt the active agents, such as greater than 70° C. and/or from about 75° C. to about 100° C. and/or from about 80° C. (in the absence of water) to form a filament-forming composition;
b. producing one or more fibrous elements and/or films from the filament-forming composition to form an article according to the present invention.

In one example, the fibrous elements and/or films of the present invention may be made by any suitable processes. A non-limiting example of a suitable process for making the fibrous elements is described below.

Figure 16:
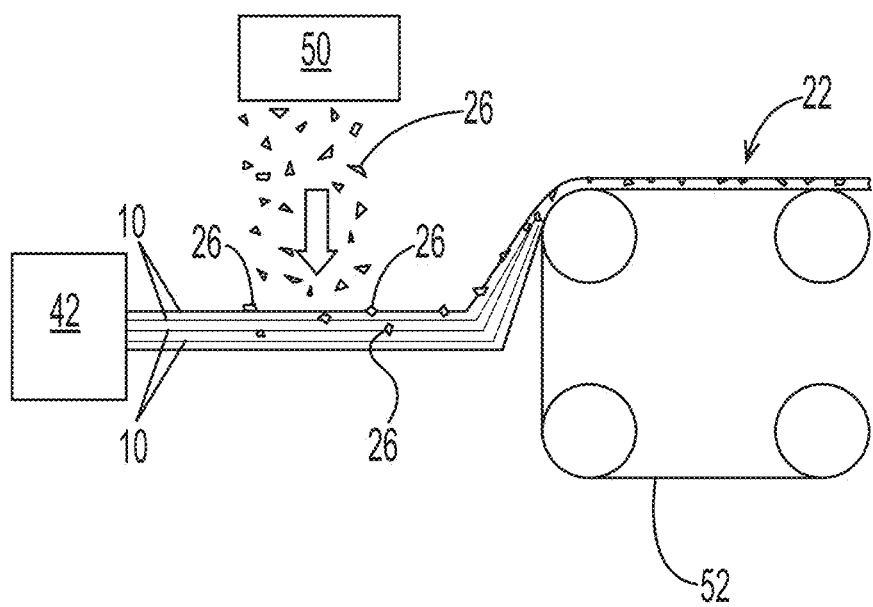
FIG. 16 is a schematic representation of an example of another process for making an example of a fibrous structure according to the present disclosure.

As shown in FIG. 16, a fibrous structure, for example a fibrous structure layer or ply 22 of the present invention may be made by spinning a filament-forming composition from a spinning die 42, as described in FIGS. 14 and 15, to form a plurality of fibrous elements, such as filaments 10, and then optionally, associating one or more particles 26 provided by a particle source 50, for example a sifter or a airlaid forming head. The particles 26 may be dispersed within the fibrous elements, for example filaments 10. The mixture of particles 26 and fibrous elements, for example filaments 10 may be collected on a collection belt 52, such as a patterned collection belt that imparts a texture, such as a three-dimensional texture to at least one surface of the fibrous structure layer or ply 22.

Figure 17:
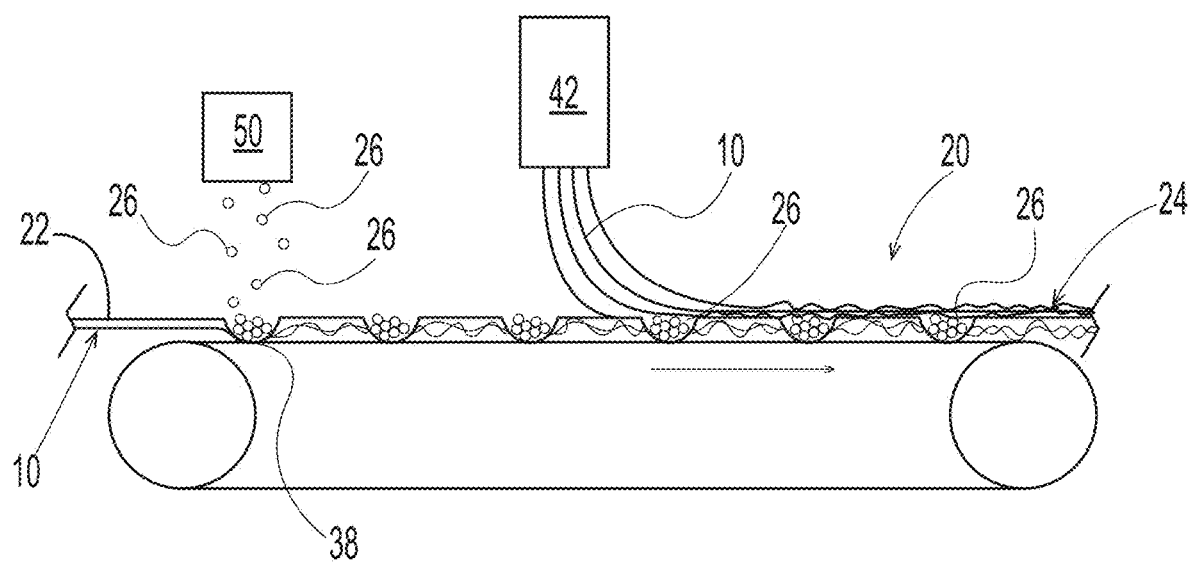
FIG. 17 is a schematic representation of another example of a process for making another example of a fibrous structure according to the present disclosure.

FIG. 17 illustrates an example of a method for making an article 20 according to FIG. 5. The method comprises the steps of forming a first fibrous structure layer 22 of a plurality of fibrous elements, for example filaments 10 such that pockets 28 are formed in a surface of the first fibrous structure layer 22. One or more particles 26 are deposited into the pockets 28 from a particle source 50. A second fibrous structure layer 24 comprising a plurality of fibrous elements, for example filaments 10 produced from a spinning die 42 are then formed on the surface of the first fibrous structure layer 22 such that the particles 26 are entrapped in the pockets 28.

Figure 18:
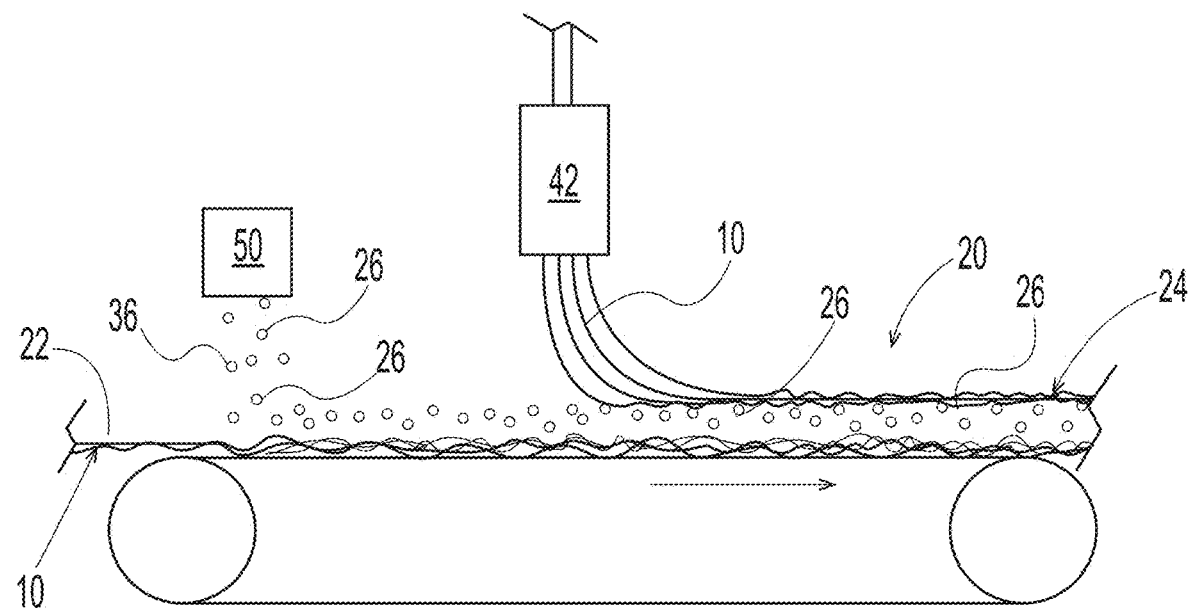
FIG. 18 is a schematic representation of another example of a process for making another example of a fibrous structure according to the present disclosure.

FIG. 18 illustrates yet another example of a method for making an article 20 according to FIG. 4. The method comprises the steps of forming a first fibrous structure layer 22 of a plurality of fibrous elements, for example filaments 10. One or more particles 26 are deposited onto a surface of the first fibrous structure layer 22 from a particle source 50. A second fibrous structure layer 24 comprising a plurality of fibrous elements, for example filaments 10 produced from a spinning die 42 are then formed on top of the particles 26 such that the particles 26 are positioned between the first fibrous structure layer 22 and the second fibrous structure layer 24.

Figure 19:
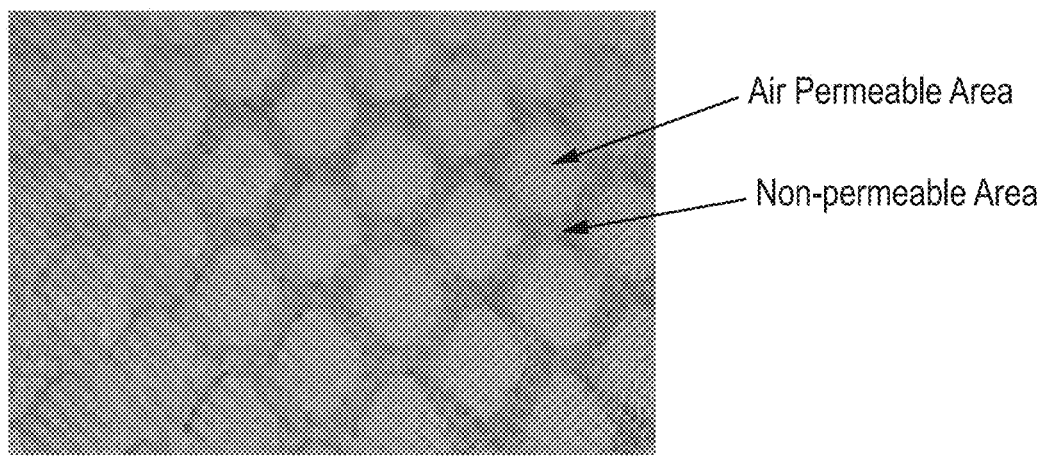
FIG. 19 is a representative image of an example of a patterned belt useful in the processes for making the fibrous structure according to the present disclosure.

The dry embryonic fibrous elements, for example filaments may be collected on a molding member as described above. The construction of the molding member may provide areas that are air-permeable due to the inherent construction. The filaments that are used to construct the molding member will be non-permeable while the void areas between the filaments will be permeable. Additionally, a pattern may be applied to the molding member to provide additional non-permeable areas which may be continuous, discontinuous, or semi-continuous in nature. A vacuum used at the point of lay down is used to help deflect fibers into the presented pattern. An example of one of these molding members is shown in FIG. 19.

In addition to the techniques described herein in forming regions within the fibrous structures having different properties (e.g., average densities), other techniques can also be applied to provide suitable results. One such example includes embossing techniques to form such regions. Suitable embossing techniques are described in U.S. Patent Application Publication Nos. 2010/0297377, 2010/0295213, 2010/0295206, 2010/0028621, and 2006/0278355.

In one example, in a multi-ply article, one or more fibrous structure plies may be formed and/or deposited directly upon an existing ply of fibrous structure to form a multi-ply fibrous structure. The two or more existing fibrous structure plies may be combined, for example via thermal bonding, gluing, embossing, aperturing, rodding, rotary knife aperturing, die cutting, die punching, needlepunching, knurling, pneumatic forming, hydraulic forming, laser cutting, tufting, and/or other mechanical combining process, with one or more other existing fibrous structure plies to form the multi-ply article of the present invention.

Package

The articles of the present invention may be enclosed in a package, individually wrapped and/or multi-article wrapped. In one example, the package exhibits a moisture barrier with a water vapor transmission rate of less than about 1.0 g $H_2O$/day/$m^2$ and/or less than about 0.5 g $H_2O$/day/$m^2$ and/or less than about 0.3 g $H_2O$/day/$m^2$ and/or about 0.1 g $H_2O$/day/$m^2$.

Method of Use

The present invention also provides for a method of using the articles of the present invention to treat fabrics, for example to provide fabric conditioning benefits to fabrics during a drying process, for example an automatic clothes dryer drying process and/or in a washing machine operation and/or to treat hair, for example to provide hair conditioning benefits to hair during a treating process. In one example, a method of treating fabrics in an automatic clothes dryer drying process comprises the step of contacting a fabric with an article according to the present invention within the dryer tub of an automatic clothes drying machine such that the fabric is treated. The step of contacting comprises the step of transferring (depositing) at least a portion of the article's mass to the fabric, for example such that the mass of article transferred to (deposited on) the fabric does not result in a stain on the fabric. It is believed that the fabric conditioning active agents are released from the article of the present invention, due in part to the tumbling action and/or the heated air of the automatic clothes dryer.

In one example, the article of the present invention is suitable for a single use, in other words, the article is a consumable, single-use article, since it is designed to disappear in the automatic clothes dryer drying process. In other words, the article, which is dry, for example dry-to-the-touch, is a dryer-added article that disappears and/or is entirely consumed and/or is entirely transferred to (deposited on) fabrics during use in the automatic clothes dryer drying process. "Dry-to-the-touch" as used herein means an article is substantially free of liquids, for example water, such that it does not feel damp or wet prior to being subjected to water or other liquids. In other words, a dry-to-the-touch article of the present invention does not contain liquids, such as water. In one non-limiting example, a dry-to-the-touch article has a water content of less than about 20% and/or less than about 15% and/or less than about 10% and/or less than about 5% and/or less than about 3% and/or less than about 1% and/or about 0% as measured according to the Water Content Test Method described herein.

In one example, the articles of the present invention may be used for imparting the fabric conditioning active agents to fabrics to provide fabric conditioning benefits such as softening, anti-static effects, and improved perfume deposition on the fabrics in an automatic clothes dryer. Generally, the method of using the articles of the present invention comprises: commingling pieces of damp and/or dry fabric by tumbling the fabrics under heat in an automatic clothes dryer with one or more articles of the present invention. In one example, the articles of the present invention exhibit a viscosity of less than about 2000 cps at 38° C. and a melting point greater than about 25° C. and/or from about 35° C. to about 100° C. such that the article is flowable at automatic clothes dryer operating temperatures.

In one example, a method of treating fabrics in a washing machine process comprises the step of contacting a fabric with an article according to the present invention within the washing machine tub such that the fabric is treated. The step of contacting comprises the step of transferring (depositing) at least a portion of the article's mass to the fabric, for example such that the mass of article transferred to (deposited on) the fabric does not result in a stain or visible residue on the fabric. It is believed that the fabric conditioning active agents are released from the article, due in part to the tumbling action and/or the water and/or heated air and/or water of the washing machine.

In one example, the article of the present invention is suitable for a single use, in other words, the article is a consumable, single-use article, since it is designed to disappear in the washing process, for example washing machine process. In other words, the article, which is dry, for example dry-to-the-touch, is a dryer-added article that disappears and/or is entirely consumed and/or is entirely transferred to (deposited on) fabrics during use in the washing process, for example washing machine process. In one example, a consumable, single use, dry-to-the-touch dryer-added article, for example wherein the consumable, single use, dry-to-the-touch dryer added article may comprise an article, product, and/or multi-article sheet according to any of the present invention is provided. In another example, a consumable, single use, water-insoluble washing machine-added article, for example wherein the consumable, single use, dry-to-the-touch dryer added article may comprise an article, product, and/or multi-article sheet according to the present invention, for example wherein the article is a dry-to-the-touch article, is provided. In another example, a consumable, single use, water-insoluble hair care article, for example wherein the consumable, single use, water-insoluble hair care article may comprise an article, product, and/or multi-article sheet according to the present invention, for example wherein the article is a dry-to-the-touch article.

While not wishing to be bound by theory, the inventors have surprisingly found the articles of the present invention provide consumers with a consumable, single-use article delivering a combination of 1) disappearing and/or being entirely consumed and/or is entirely transferred to (deposited on) fabrics or other treated surfaces, 2) being dry-to-the-touch, and 3) leaving behind no visible residue on the treated surface. The inventors have also discovered articles of the present invention may also be designed so as they are shippable in efficient e-commerce friendly configurations.

In one example, the articles of the present invention may be used for imparting the fabric conditioning active agents to fabrics to provide fabric conditioning benefits such as softening, anti-static effects, and improved perfume deposition on the fabrics in a washing machine. Generally, the method of using the articles of the present invention comprises: commingling pieces of damp and/or wet fabrics by agitating and/or spinning and/or tumbling the fabrics in the presence of a wash liquor, for example water and optionally detergent, and optionally in the presence of heat in a washing machine with one or more articles of the present invention. In one example, the articles of the present invention exhibit a viscosity of less than about 2000 cps at 38° C. and a melting point greater than about 25° C. and/or from about 35° C. to about 100° C. such that the article is flowable under washing machine operating conditions and/or exhibits a lamellar structure (exhibits a lamellar structure response) as measured according to the Lamellar Structure Test Method.

In still another example, the articles of the present invention may be massaged and/or kneaded into one's hair during a shampooing and/or conditioning operation for treating one's hair. In one example, the articles of the present invention exhibit a viscosity of less than about 2000 cps at 38° C. and a melting point greater than about 25° C. and/or from about 35° C. to about 100° C. such that the article is flowable under hair shampooing and/or hair conditioning operating conditions and/or exhibits a lamellar structure (exhibits a lamellar structure response) as measured according to the Lamellar Structure Test Method.

Non-Limiting Examples

Non-limiting examples of articles made from the filament-forming compositions of the present invention as shown in Table 1 below are made as follows:

a. adding one or more active agents to a metal beaker;

b. heating the metal beaker to 80° C. with stirring/agitation until a homogeneous fluid of active agents is formed;

c. maintaining the metal beaker at 80° C.; and d. adding an auxiliary ingredient (filament-forming material, such as a structurant) to the homogeneous fluid of active agents with stirring/agitation until the auxiliary ingredient is homogeneously dispersed and/or homogeneously dissolved within the homogeneous fluid of active agents resulting in a filament-forming composition that is ready for spinning into fibrous elements to form a fibrous structure and ultimately an article; and e. optionally adding optional ingredients, such as perfumes, for example perfume microcapsules, tackifiers, such as microcrystalline waxes to facilitate attaching the article to the interior dryer drum, and other optional ingredients.

In one example, the is suitable for attaching to an internal surface of an automatic clothes dryer, for example wherein the article comprises an adhesive on at least one surface.

TABLE 1

| Filament-Forming Composition/ Fibrous Element and/or Film and/or Article | Fabric Conditioning Active Agents ||||| Auxiliary Ingredients Filament-forming material (Structurant) A - Polyvinyl pyrrolidone PVP K90 OR B - Polyvinyl pyrrolidone PVP K120 |
|---|---|---|---|---|---|---|
| | Quaternary Ammonium Compound A - Di(tallow oxyethyl) hydroxyethylmethyl ammoniummethylsulfate OR B - behenyl trimonium methosulfate | Fatty Fabric Conditioning Active Agents || Nonionic surfactant Alkyl glucamide | Optional Ingredients Tackifier Microcrystalline wax w835 | |
| | | Stearic acid | Cetyl Alcohol/Stearyl Alcohol | | | |
| Example 1 | 67% by wt A | 30% by wt | — | — | — | 3% by wt A |
| Example 2 | 98% by wt A | — | — | — | — | 2% by wt A |
| Example 3 | 50% by wt A | 45% by wt | — | — | — | 5% by wt A |
| Example 4 | 70% by wt A | 6% by wt | — | — | 20% by wt | 4% by wt A |
| Example 5 | 66% by wt A | — | 32% by wt/ 0% by wt | — | — | 2% by wt A |
| Example 6 | 63% by wt A | 32% by wt | — | — | — | 5% by wt B |
| Example 7 | 25% by wt B | — | 18% by wt/ 44% by wt | 9% by wt | — | 4% by wt B |

Tables 2 and 3 below show the properties of the articles of Examples 6 and 7. In addition, Table 3 also shows some of the properties of a control article; namely, a commercially available in 2017 Bounce® dryer sheet.

TABLE 2

| Filament-Forming Composition/ Fibrous Element and/or Film and/or Article | Article Width | Article Length | Article Height | Air Permeability |
|---|---|---|---|---|
| Example 6 | 10.00 cm | 10.00 cm | 0.94 mm | 1400 L/m²/s |
| Example 7 | 10.00 cm | 10.00 cm | 1.73 mm | 452 L/m²/s |

TABLE 3

| Filament-Forming Composition/Fibrous Element and/or Film and/or Article | Article Volume | Article Mass | Article Density | Article Free Melt Flow | Dry Lamellar Structure as measured according to Lamellar Structure Test Method | Wet Lamellar Structure as measured according to Lamellar Structure Test Method |
|---|---|---|---|---|---|---|
| Example 6 | 9.40 cm³ | 1.30 g | 0.14 g/cm³ | 99% | — | — |
| Example 7 | 17.30 cm³ | 3.10 g | 0.18 g/cm³ | 75% | No | Yes |
| Bounce ® Dryer Sheet | — | 1.79 g | — | 0.56% | — | — |

Test Methods

Unless otherwise specified, all tests described herein including those described under the Definitions section and the following test methods are conducted on samples that have been conditioned in a conditioned room at a temperature of 23° C.±1.0° C. and a relative humidity of 50%±2% for a minimum of 2 hours prior to the test. The samples tested are "usable units." "Usable units" as used herein means sheets, flats from roll stock, pre-converted flats, and/or single or multi-ply products. All tests are conducted under the same environmental conditions and in such conditioned room. Do not test samples that have defects such as wrinkles, tears, holes, and like. Samples conditioned as described herein are considered dry samples (such as "dry filaments") for testing purposes. All instruments are calibrated according to manufacturer's specifications.

Width and Length Test Method

The length and width of articles having a regular shape (e.g. square, rectangle, circle, oval, etc.) are measured according to their conventional definitions. For articles of irregular shape, the article length may be defined as the maximum feret or caliper diameter, which is the longest distance between two parallel planes tangential to the boundary of the article. The article width of an irregularly shaped article may be defined as the minimum feret or caliper diameter, which is the shortest distance between two parallel planes tangential to the boundary of the article. The article length and width may be measured by any appropriate instrument that is calibrated, NIST traceable, and capable of measurements to the nearest 0.01 cm. Measure and record the length and width of ten (10) substantially similar replicate articles. Average together the 10 individual article length measurements and report the value to the nearest 0.01 cm. Average together the 10 individual article width measurements and report the value to the nearest 0.01 cm.

Height Test Method

The height of an article is measured using a ProGage Thickness Tester (Thwing-Albert Instrument Company, West Berlin, N.J.) with a circular pressure foot diameter of 2.00 inches (area of 3.14 in²) at a pressure of 15.5 g/cm². Ten (10) samples are prepared by cutting samples of a planar article such that each cut sample is larger in size than the pressure foot surface, avoiding creases, folds, and obvious defects. If an article has a length or width less than the diameter of the pressure foot a smaller diameter pressure foot may be used, while making the appropriate adjustments so that a pressure of 15.5 g/cm² is still applied. An individual sample is placed on the anvil with the sample centered underneath the pressure foot, or centered on the location of the maximum height of an article. The foot is lowered at 0.03 in/sec to an applied pressure of 15.5 g/cm². The reading is taken after a 3 second dwell time, and the foot is raised. The measure is repeated in like fashion for the remaining 9 samples. The thickness or article height is calculated as the average thickness of the ten samples and is reported to the nearest 0.01 mm.

Volume Test Method

The volume of an article is calculated by measuring the projected area of the article, as viewed orthogonally to the plane of the article length and width, in square centimeters, as measured according to the Width and Length Test Method described herein, and then multiplying it by the height of the article in centimeters as measured by the Height Test Method described herein. Measure and record the volume often (10) substantially similar replicate articles. Average together the 10 individual article volume measurements and report the value to the nearest 0.01 cubic centimeters (cm³).

Mass Test Method

The mass of an article is measured using a top loading analytical balance with a resolution of ±0.01 g, and is protected from air drafts and other disturbances using a draft shield. Prior to taking the mass measurement, properly condition the article as previously described. After conditioning, measure the mass of the article to the nearest 0.01 g. Measure and record the mass of ten (10) substantially similar replicate articles. Average together the 10 individual article mass measurements and report the value to the nearest 0.01 g.

Density Test Method

The density of an article ("article density") is calculated by dividing the article mass by the article volume. The article density is reported to the nearest 0.01 g/cm³.

Basis Weight Test Method

The basis weight of an article is calculated by dividing the article mass by the projected area of the article as viewed orthogonally to the plane of the article length and width. The article basis weight is reported to the nearest 0.01 g/m².

Tensile Test Method: Elongation, Tensile Strength, TEA and Modulus

Elongation, Tensile Strength, TEA and Tangent Modulus are measured on a constant rate of extension tensile tester with computer interface (a suitable instrument is the EJA Vantage from the Thwing-Albert Instrument Co. Wet Berlin, N.J.) using a load cell for which the forces measured are within 10% to 90% of the limit of the cell. Both the movable (upper) and stationary (lower) pneumatic jaws are fitted with smooth stainless steel faced grips, 25.4 mm in height and wider than the width of the test specimen. An air pressure of about 60 psi is supplied to the jaws.

Eight usable units of a fibrous structure, or article sheet are divided into two stacks of four samples each. The samples in each stack are consistently oriented with respect to machine direction (MD) and cross direction (CD). One of the stacks is designated for testing in the MD and the other for CD. Using a one inch precision cutter (Thwing Albert JDC-1-10, or similar) cut 4 MD strips from one stack, and 4 CD strips from the other, with dimensions of 1.00 in +0.01 in wide by 3.0-4.0 in long. Each strip of one usable unit thick will be treated as a unitary specimen for testing.

Program the tensile tester to perform an extension test, collecting force and extension data at an acquisition rate of 20 Hz as the crosshead raises at a rate of 2.00 in/min (5.08 cm/min) until the specimen breaks. The break sensitivity is set to 80%, i.e., the test is terminated when the measured force drops to 20% of the maximum peak force, after which the crosshead is returned to its original position.

Set the gauge length to 1.00 inch. Zero the crosshead and load cell. Insert at least 1.0 in of the unitary specimen into the upper grip, aligning it vertically within the upper and lower jaws and close the upper grips. Insert the unitary specimen into the lower grips and close. The unitary specimen should be under enough tension to eliminate any slack, but less than 5.0 g of force on the load cell. Start the tensile tester and data collection. Repeat testing in like fashion for all four CD and four MD unitary specimens. Program the software to calculate the following from the constructed force (g) verses extension (in) curve:

Tensile Strength is the maximum peak force (g) divided by the sample width (in) and reported as g/in to the nearest 1 g/in.

Adjusted Gauge Length is calculated as the extension measured at 3.0 g of force (in) added to the original gauge length (in).

Elongation is calculated as the extension at maximum peak force (in) divided by the Adjusted Gauge Length (in) multiplied by 100 and reported as % to the nearest 0.1%

Total Energy (TEA) is calculated as the area under the force curve integrated from zero extension to the extension at the maximum peak force (g*in), divided by the product of the adjusted Gauge Length (in) and specimen width (in) and is reported out to the nearest 1 g*in/in$^2$.

Replot the force (g) verses extension (in) curve as a force (g) verses strain curve. Strain is herein defined as the extension (in) divided by the Adjusted Gauge Length (in). Program the software to calculate the following from the constructed force (g) verses strain curve:

Tangent Modulus is calculated as the slope of the linear line drawn between the two data points on the force (g) versus strain curve, where one of the data points used is the first data point recorded after 28 g force, and the other data point used is the first data point recorded after 48 g force. This slope is then divided by the specimen width (2.54 cm) and reported to the nearest 1 g/cm.

The Tensile Strength (g/in), Elongation (%), Total Energy (g*in/in$^2$) and Tangent Modulus (g/cm) are calculated for the four CD unitary specimens and the four MD unitary specimens. Calculate an average for each parameter separately for the CD and MD specimens.

Calculations:

Geometric Mean Tensile=Square Root of [MD Tensile Strength (g/in)×CD Tensile Strength (g/in)]

Geometric Mean Peak Elongation=Square Root of [MD Elongation (%)×CD Elongation (%)]

Geometric Mean TEA=Square Root of [MD TEA (g*in/in$^2$)×CD TEA (g/in$^2$)]

Geometric Mean Modulus=Square Root of [MD Modulus (g/cm)×CD Modulus (g/cm)]

Total Dry Tensile Strength (TDT)=MD Tensile Strength (g/in)+CD Tensile Strength (g/in)

Total TEA=MD TEA (g*in/in$^2$)+CD TEA (g*in/in$^2$)

Total Modulus=MD Modulus (g/cm)+CD Modulus (g/cm)

Tensile Ratio=MD Tensile Strength (g/in)/CD Tensile Strength (g/in)

Water Content Test Method

The water (moisture) content present in an article is measured using the following Water Content Test Method. An article sample, or portion thereof, is placed in a conditioned room at a temperature of 23° C.±1.0 C.° and a relative humidity of 50%±2% for at least 24 hours prior to testing. Under the temperature and humidity conditions mentioned above, using a balance with at least four decimal places, the weight of the sample is recorded every five minutes until a change of less than 0.5% of previous weight is detected during a 10 minute period. The final weight is recorded as the "equilibrium weight". Within 10 minutes, the samples are placed into a forced air oven on top of foil, or inside an aluminum tray for 24 hours at 70° C.±2 C° at a relative humidity of 4%±2% for drying. After the 24 hours of drying, the sample is removed and weighed within 15 seconds. This weight is designated as the "dry weight" of the sample. The water (moisture) content of the sample is calculated according to the following equation:

$$\% \text{ Water Content} = \frac{\text{Equilibrium Weight} - \text{Dry Weight}}{\text{Dry Weight}} \times 100$$

The % Water Content is measured for 3 replicate samples, and averaged to give the reported to the nearest 0.1%.

Median Particle Size Test Method

This test method must be used to determine median particle size.

The median particle size test is conducted to determine the median particle size of the seed material using ASTM D 502-89, "Standard Test Method for Particle Size of Soaps and Other Detergents", approved May 26, 1989, with a further specification for sieve sizes used in the analysis. Following section 7, "Procedure using machine-sieving method," a nest of clean dry sieves containing U.S. Standard (ASTM E 11) sieves #8 (2360 um), #12 (1700 um), #16 (1180 um), #20 (850 um), #30 (600 um), #40 (425 um), #50 (300 um), #70 (212 um), #100 (150 um) is required. The prescribed Machine-Sieving Method is used with the above sieve nest. The seed material is used as the sample. A suitable sieve-shaking machine can be obtained from W. S. Tyler Company of Mentor, Ohio, U.S.A.

The data are plotted on a semi-log plot with the micron size opening of each sieve plotted against the logarithmic abscissa and the cumulative mass percent ($Q_3$) plotted against the linear ordinate. An example of the above data representation is given in ISO 9276-1:1998, "Representation of results of particle size analysis—Part 1: Graphical Representation", FIG. A.4. The seed material median particle size ($D_{50}$), for the purpose of the present disclosure, is defined as the abscissa value at the point where the cumulative mass percent is equal to 50 percent, and is calculated by a straight line interpolation between the data points directly above (a50) and below (b50) the 50% value using the following equation:

$$D_{50}=10^{[\text{Log}(D_{a50})-(\text{Log}(D_{a50})-\text{Log}(D_{b50}))*(Q_{a50}-50\%)/(Q_{a50}-Q_{b50})]}$$

where $Q_{a50}$ and $Q_{b50}$ are the cumulative mass percentile values of the data immediately above and below the 50$^{th}$ percentile, respectively; and $D_{a50}$ and $D_{b50}$ are the micron sieve size values corresponding to these data.

In the event that the $50^{th}$ percentile value falls below the finest sieve size (150 um) or above the coarsest sieve size (2360 um), then additional sieves must be added to the nest following a geometric progression of not greater than 1.5, until the median falls between two measured sieve sizes.

The Distribution Span of the Seed Material is a measure of the breadth of the seed size distribution about the median. It is calculated according to the following:

$$\text{Span}=(D_{84}/D_{50}+D_{50}/D_{16})/2$$

Where $D_{50}$ is the median particle size and $D_{84}$ and $D_{16}$ are the particle sizes at the sixteenth and eighty-fourth percentiles on the cumulative mass percent retained plot, respectively.

In the event that the $D_{16}$ value falls below the finest sieve size (150 um), then the span is calculated according to the following:

$$\text{Span}=(D_{84}/D_{50}).$$

In the event that the $D_{84}$ value falls above the coarsest sieve size (2360 um), then the span is calculated according to the following:

$$\text{Span}=(D_{50}/D_{16}).$$

In the event that the $D_{16}$ value falls below the finest sieve size (150 um) and the $D_{84}$ value falls above the coarsest sieve size (2360 um), then the distribution span is taken to be a maximum value of 5.7.

Diameter Test Method

The diameter of a discrete fibrous element or a fibrous element within a fibrous structure is determined by using a Scanning Electron Microscope (SEM) or an Optical Microscope and an image analysis software. A magnification of 200 to 10,000 times is chosen such that the fibrous elements are suitably enlarged for measurement. When using the SEM, the samples are sputtered with gold or a palladium compound to avoid electric charging and vibrations of the fibrous element in the electron beam. A manual procedure for determining the fibrous element diameters is used from the image (on monitor screen) taken with the SEM or the optical microscope. Using a mouse and a cursor tool, the edge of a randomly selected fibrous element is sought and then measured across its width (i.e., perpendicular to fibrous element direction at that point) to the other edge of the fibrous element. A scaled and calibrated image analysis tool provides the scaling to get actual reading in μm. For fibrous elements within a fibrous structure, several fibrous elements are randomly selected across the sample of the fibrous structure using the SEM or the optical microscope. At least two portions of the fibrous structure are cut and tested in this manner. Altogether at least 100 such measurements are made and then all data are recorded for statistical analysis. The recorded data are used to calculate average (mean) of the fibrous element diameters, standard deviation of the fibrous element diameters, and median of the fibrous element diameters.

Another useful statistic is the calculation of the amount of the population of fibrous elements that is below a certain upper limit. To determine this statistic, the software is programmed to count how many results of the fibrous element diameters are below an upper limit and that count (divided by total number of data and multiplied by 100%) is reported in percent as percent below the upper limit, such as percent below 1 micrometer diameter or %-submicron, for example. We denote the measured diameter (in μm) of an individual circular fibrous element as di.

In the case that the fibrous elements have non-circular cross-sections, the measurement of the fibrous element diameter is determined as and set equal to the hydraulic diameter which is four times the cross-sectional area of the fibrous element divided by the perimeter of the cross-section of the fibrous element (outer perimeter in case of hollow fibrous elements). The number-average diameter, alternatively average diameter is calculated as:

$$d_{num} = \frac{\sum_{i=1}^{n} d_i}{n}$$

Air Permeability Test Method

The Air Permeability Parameter is determined using the Air Permeability Test Method, which is based on EDANA 140.1-99. In the Air Permeability Test Method, three specimens from three separate articles are interrogated with an air permeability device that measures the air flow through a specimen required to maintain a preset pressure difference across that same specimen. All measurements are done at 50±5% relative humidity and 23±2° C., and all samples are equilibrated in this same environment for at least twelve hours prior to testing.

Three specimens are prepared, each from one of three representative articles. Each specimen is a circular disc 5 cm in diameter centered on the intersection of the longitudinal and lateral centerlines of the article.

Air permeability is determined using the Textest FX3300 LabAir III (Textest AG, Schwerzenbach, Switzerland) or equivalent instrument outfitted with a circular 5 cm² test head (diameter=2.52 cm). In this configuration, the instrument is capable of measuring air flow rates per unit area of between 4 liters per square meter per second (L/m²/s) and 7500 L/m²/s at a pressure differential of 125 Pa. The instrument is powered on and calibrated with a calibration plate according to the manufacturer's instructions. The differential pressure for all measurements is set to 125 Pa. Each specimen is then measured by placing it (centered) within the test head such that the air pathway is completely covered by the specimen and recording the resulting steady-state air flow rate to three significant figures. (If fewer than three significant figures are displayed on the instrument readout, the air flow rate is recorded to the number of significant figures displayed.) The resulting air flow rate for each specimen is divided by the area of the test head (5 cm²) to obtain a flow rate per unit area in L/m²/s. If the specimen has insufficient permeability to allow for a measurable air flow rate at a differential pressure of 125 Pa, the air flow rate per unit area is defined to be 4 L/m²/s. If the specimen has permeability so high such that 125 Pa of differential pressure cannot be maintained even at the high end of the instrument's volumetric flow range, the air flow rate per unit area is defined to be 7500 L/m²/s. The arithmetic mean of the air flow rates per unit area from each of the three specimens is defined as the Air Permeability Parameter and is reported to 3 significant figures.

Free Melt Flow Test Method

The Free Melt Flow Parameter is determined using the Free Melt Flow Test Method. In this method, a specimen taken from an article(s) is held at an elevated temperature for an extended period of time in close proximity to an absorbent medium, and the propensity of material from the article to melt, flow, and be absorbed by the absorbent medium is quantified.

The ambient conditions of the laboratory are 23±2° C. and 40±10% relative humidity. Seven sheets of 150-mm diameter Grade 4 filter paper (such as Whatman 1004-150, GE Healthcare Bio-Sciences, or equivalent) are stacked and the mass is recorded to within ±0.01 g. This is the initial filter paper mass. The stack of filter paper is then placed onto a stainless steel grating (the lower grating) that extends beyond the 150-mm outer diameter of the filter paper. The grating is composed of solid parallel rods 3.4 mm in diameter and spaced 12.5 mm on center in a planar configuration. The grating comprises a frame or end rails to hold the rods in place, with the frame or rails beyond the outer edges of the filter paper. An identical grating (the upper grating) is then placed on top of the stack of filter paper such that the filter paper is captive between the two gratings (the grating assembly). The upper and lower gratings are oriented such that the constituent rods of the two gratings are parallel to each other and "registered" such that the rods of the two gratings are directly above one another in a vertical direction.

The mass of the specimen to be analyzed is 2.0±0.1 g, measured to within ±0.01 g. A 50 mm×50 mm square of material is cut from the center of the article. If this 50 mm×50 mm square weighs 2.0±0.1 g, it is the specimen used for the analysis. If this 50 mm×50 mm square weighs more than 2.1 g, it is resampled in its center with a smaller square of mass 2.0±0.1 g, and this resulting smaller square is the specimen used for the analysis. If this 50 mm×50 mm square weighs less than 1.9 g, additional 50 mm×50 mm squares are cut from the centers of like articles and stacked until the total mass is 2.0±0.1 g, and this stack is the specimen used for the analysis. (In this case, the final 50 mm×50 mm square used may be subsampled in its center in order to achieve the specified target mass of the specimen.) The specimen is then placed on the top grating such that it is centered over the stack of filter paper. This entire assembly is then placed (such that in an oven held at 80° C. for a duration of 24.0 hours. The racks are supported such that there is free space above the specimen and below the lower grating where the 150 mm-diameter filter paper is positioned (that is, the lower grating is not resting on the oven floor).

At the end of the 24-hour period, the grating assembly is removed from the oven, and the filter paper is removed from the between the lower and upper gratings and allowed to re-equilibrate for 1 hour to ambient lab conditions. The mass of the filter paper along with any absorbed material from the article, defined as the final filter paper mass, is then determined to within ±0.01 g. The Free Melt Flow Parameter is calculated according to the equation below:

$$\text{Free Melt Flow Parameter} = \frac{100\% \times (\text{Final Filter Paper Mass} - \text{Initial Filter Paper Mass})}{\text{Specimen Mass}}$$

The Free Melt Flow Parameter is reported as a percent rounded to the nearest integer percent value.

Lamellar Structure Test Method

The Lamellar Structure Test Method makes use of small-angle x-ray scattering (SAXS) to determine if a lamellar structure is present in an article either in a conditioned, dry state or upon wetting after having been previously in a conditioned, dry state. Fibrous material articles are conditioned at a temperature of 23° C.±2.0° C. and a relative humidity of 40%±10% for a minimum of 12 hours prior to the test. Articles conditioned as described herein are considered to be in a conditioned, dry state for the purposes of this invention. All instruments are calibrated according to manufacturer's specifications.

Dry Sample Preparation

To prepare a sample to be analyzed directly in the conditioned, dry state, a specimen of about 1.0 cm diameter disc is isolated from the center of an article and is loaded into a conventional SAXS solid sample holder with aperture diameter between 4 and 5 mm. Multiple specimen discs may be extracted from multiple articles and stacked, if necessary, to ensure sufficient scattering cross-section. The loaded sample holder is immediately placed in the appropriate instrument for data collection.

Wet Sample Preparation

Three samples are analyzed upon wetting from the dry, conditioned state. Specimens are extracted from dry, conditioned articles and hydrated with water in order to achieve three separate preparations each possessing a different specimen-to-water mass ratio. The three different specimen-to-water mass ratios to be prepared are 1:5, 1:9, and 1:20. For each mass ratio, one or more specimens (as needed) 1 cm in diameter are extracted from the geometric centers of one or more articles in the dry, conditioned state are hydrated with 23° C.±2.0° C. filtered deionized (DI) water in order to achieve the intended specimen-to-water mass ratio. Each of the three specimen/water mixtures (each corresponding to a different mass ratio) is stirred under low shear gently by hand at room temperature using a spatula until visibly homogenous. Each specimen/water mixture is then immediately loaded into a separate quartz capillary tube with outer diameter 2.0 mm in diameter and 0.01 mm wall thickness. The capillary tubes are immediately sealed with a sealant such as an epoxy resin to prevent the evaporation of water from the preparations. The sealant is permitted to dry for at least 2 hours and until dry at a temperature of 23° C.±2.0° C. prior to sample analysis. Each prepared wet sample is introduced into an appropriate SAXS instrument and data are collected.

Testing and Analysis

Samples are tested using SAXS in 2-dimension (2D) transmission mode over an angular range in of 0.3° to 3.0° 2θ, to observe the presence and spacing of any intensity bands in the x-ray scattering pattern. The test is conducted using a SAXS instrument (such as the NanoSTAR, Bruker AXS Inc., Madison, Wis., U.S.A., or equivalent). Conditioned, dry samples are analyzed under ambient pressure. Sealed liquid samples are analyzed in the instrument under vacuum. All samples are analyzed at a temperature of 23° C.±2.0° C. The x-ray tube of the instrument is operated at sufficient power to ensure that any scattering bands present are clearly detected. The beam diameter is 550±50 µm. One suitable set of operating conditions includes the following selections: NanoSTAR instrument; micro-focus Cu x-ray tube using the Kα line at 1.54 Å; 45 kV and 0.650 mA power; Vantec2K 2-Dimensional area detector; collection time of 1200 seconds; and distance between the sample and detector of 112.050 cm. The raw 2-D SAXS scattering pattern is integrated azimuthally to determine intensity (I) as a function of the scattering vector (q), which are expressed throughout this method units of reciprocal angstroms (Å$^{-1}$). The values for q are calculated by the SAXS instrument according to the following equation:

$$q = \frac{4\pi}{\lambda}\sin\theta$$

where:
2θ is the scattering angle; and
λ is the wavelength used.

For each integrated SAXS analyzed, the value of q in Å$^{-1}$ corresponding to each intensity peak on the plot of I vs q is identified and recorded from smallest to largest. (One of skill in the art knows that a sharp peak in q near the origin corresponds to scatter off of the beam stop and is disregarded in this method.) The value of q corresponding to the first intensity peak (the lowest value of q) is referred to as q*.

For a sample corresponding to a specimen (taken from a fibrous material article) analyzed directly in the dry, conditioned state, if an intensity peak is present at 2q*±0.002 Å$^{-1}$, then the fibrous material of which the article is composed is determined to exhibit a lamellar structure, and the characteristic d-spacing parameter is defined as 2π/q*. If no intensity peak is present at 2q*±0.002 Å$^{-1}$, then the fibrous material of which the article is composed is determined to not exhibit a lamellar structure.

For a sample analyzed upon wetting from the dry, conditioned state, if an intensity peak is present at 2q*±0.002 Å$^{-1}$, the sample is determined to exhibit a lamellar structure, and the characteristic d-spacing parameter is defined as 2π/q*. If no intensity peak is present at 2q*±0.002 Å$^{-1}$, the sample is determined to not exhibit a lamellar structure. If a lamellar structure is determined to be present in at least any one of the three specimen/water ratios prepared, then the material of which the articles are composed is determined to exhibit a lamellar structure upon wetting. If no intensity peak is present at 2q*±0.002 Å$^{-1}$, in any of the three specimen/water ratios prepared, then the material of which the articles are composed is determined to not exhibit a lamellar structure upon wetting.

Fibrous Element Composition Test Method

In order to prepare fibrous elements for fibrous element composition measurement, the fibrous elements must be conditioned by removing any coating compositions and/or materials present on the external surfaces of the fibrous elements that are removable. An example of a method for doing so is washing the fibrous elements 3 times with a suitable solvent that will remove the external coating while leaving the fibrous elements unaltered. The fibrous elements are then air dried at 23° C.±1.0° C. until the fibrous elements comprise less than 10% moisture. A chemical analysis of the conditioned fibrous elements is then completed to determine the compositional make-up of the fibrous elements with respect to the filament-forming materials and the active agents and the level of the filament-forming materials and active agents present in the fibrous elements.

The compositional make-up of the fibrous elements with respect to the filament-forming material and the active agents can also be determined by completing a cross-section analysis using TOF-SIMs or SEM. Still another method for determining compositional make-up of the fibrous elements uses a fluorescent dye as a marker. In addition, as always, a manufacturer of fibrous elements should know the compositions of their fibrous elements.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A consumable, single use solid article comprising:
   a. one or more active agents present in the consumable, single use solid article; and
   b. one or more auxiliary ingredients;
   wherein the consumable, single use solid article disappears during automatic clothes dryer use;
   wherein the consumable, single use solid article exhibits an article density of less than about 0.80 g/cm$^3$ as measured according to the density test method; and
   wherein the consumable, single use solid article exhibits a free melt flow of more than about 20% as measured according to the free melt flow test method.

2. The consumable, single use solid article according to claim 1 wherein the consumable, single use solid article comprises greater than 90% by weight of the one or more active agents.

3. The consumable, single use solid article according to claim 1 wherein at least one of the one or more active agents comprises a fabric conditioning active agent.

4. The consumable, single use solid article according to claim 3 wherein the fabric conditioning active agent is selected from the group consisting of: fatty acids, fatty acid derivatives, sulfonic acid derivatives, quaternary ammonium compounds, tertiary amines and salts thereof, nonionic surfactants, fatty alcohols, and mixtures thereof.

5. The consumable, single use solid article according to claim 4 wherein the fabric conditioning active agent comprises a fatty acid selected from the group consisting of: myristic acid, stearic acid, isostearic acid, cetearic acid, dodecanoic acid, linoleic acid, oleic acid, palmitic acid, lauric acid, and mixtures thereof.

6. The consumable, single use solid article according to claim 4 wherein the fabric conditioning active agent comprises a quaternary ammonium compound selected from the group consisting of: di(tallowyloxyethyl)hydroxyethylmethylammoniummethylsulfate, dimethyl bis(stearoyl oxyethyl) ammonium chloride, dimethyl bis(tallowyloxyethyl)ammonium chloride, dimethyl bis(tallowyloxyisopropyl) ammonium methylsulfate, and mixtures thereof.

7. The consumable, single use solid article according to claim 4 wherein the fabric conditioning active agent comprises a fatty alcohol selected from the group consisting of:

cetyl alcohol, stearyl alcohol, behenyl alcohol, lauryl alcohol, myristic alcohol, isostearyl alcohol, arachidyl alcohol, and mixtures thereof.

8. The consumable, single use solid article according to claim 4 wherein the fabric conditioning active agent comprises a fatty alcohol and a quaternary ammonium compound.

9. The consumable, single use solid article according to claim 8 wherein the fatty alcohol and quaternary ammonium compound are present in the solid article at a weight ratio of greater than 1:1.

10. The consumable, single use solid article according to claim 4 wherein the fabric conditioning active agent comprises a fatty acid and a quaternary ammonium compound.

11. The consumable, single use solid article according to claim 10 wherein the fatty acid and quaternary ammonium compound are present in the solid article at a weight ratio of greater than 1:1.

12. The consumable, single use solid article according to claim 1 wherein at least one of the one or more active agents is selected from the group consisting of: fabric care active agents, dishwashing active agents, carpet care active agents, surface care active agents, hair care active agents, air care active agents, oral care active agents, dryer added active agents, and mixtures thereof.

13. The consumable, single use solid article according to claim 12 wherein at least one of the one or more active agents is selected from the group consisting of: perfumes, builders, chelants, antioxidants, brighteners, sun fade inhibiting agents, UV absorbing agents, insect repellants, scents, bleaching agents, enzymes, antimicrobials, antibacterials, antifungals, perfume delivery systems, perfume microcapsules, dye transfer inhibiting agents, hueing dyes, soil release agents, colorants, preservatives, opacifiers, stabilizers, anti-shrinkage agents, anti-wrinkle agents, fabric crisping agents, reductive agents, spotting agents, germicides, fungicides, anti-corrosion agents, and mixtures thereof.

14. The consumable, single use solid article according to claim 1 wherein at least one of the one or more auxiliary ingredients comprises a structurant.

15. The consumable, single use solid article according to claim 1 wherein at least one of the one or more auxiliary ingredients is dispersed throughout the one or more active agents.

16. The consumable, single use solid article according to claim 1 wherein the consumable, single use solid article comprises one or more fibrous elements.

17. The consumable, single use solid article according to claim 1 wherein the consumable, single use solid article exhibits one or more of the following characteristics:
    a. a width from about 1 cm to about 15 cm;
    b. a length from about 1 cm to about 23 cm;
    c. a height from about 0.01 mm to about 50 mm;
    d. a mass from about 0.10 g to about 10 g;
    e. a volume from about 0.25 cm$^3$ to about 60.00 cm$^3$; and
    f. a density from about 0.05 g/cm$^3$ to about 0.80 g/cm$^3$.

18. The consumable, single use solid article according to claim 1 wherein the consumable, single use solid article exhibits a lamellar structure response as measured according to the lamellar structure test method.

19. The consumable, single use solid article according to claim 1 wherein the consumable, single use solid article exhibits a lamellar structure response in a wet state but does not exhibit a lamellar structure response in a dry state as measured according to the lamellar structure test method.

* * * * *